US 6,721,310 B2

(12) United States Patent
Liu et al.

(10) Patent No.: US 6,721,310 B2
(45) Date of Patent: Apr. 13, 2004

(54) MULTIPORT NON-BLOCKING HIGH CAPACITY ATM AND PACKET SWITCH

(75) Inventors: Zheng Liu, Saratoga, CA (US); Jiu An, San Jose, CA (US); Terry Xian, Fremont, CA (US); Ronald P. Novick, Orange, CT (US)

(73) Assignee: TranSwitch Corporation, Shelton, CT (US)

( * ) Notice: Subject to any disclaimer, the term of this patent is extended or adjusted under 35 U.S.C. 154(b) by 0 days.

(21) Appl. No.: 10/000,272

(22) Filed: Nov. 2, 2001

(65) Prior Publication Data

US 2003/0099193 A1 May 29, 2003

(51) Int. Cl.[7] ............................................. H04L 12/28
(52) U.S. Cl. .................. 370/362; 370/352; 709/253
(58) Field of Search ............................... 370/352, 357, 370/362, 365, 370; 709/253

(56) References Cited

U.S. PATENT DOCUMENTS

| | | | | |
|---|---|---|---|---|
| 4,154,983 A | * | 5/1979 | Pedersen ..................... | 370/352 |
| 4,922,244 A | | 5/1990 | Hullett et al. ............. | 340/825.5 |
| 4,977,557 A | | 12/1990 | Phung et al. ................ | 370/85.6 |
| 5,001,707 A | | 3/1991 | Kositpaiboom ............ | 370/94.1 |
| 5,121,388 A | | 6/1992 | Perdikaris .................. | 370/85.4 |
| 5,208,805 A | | 5/1993 | Ochiai ......................... | 370/60 |
| 5,210,750 A | | 5/1993 | Nassehi et al. ............. | 370/85.2 |
| 5,402,422 A | | 3/1995 | Liu et al. ..................... | 370/85.5 |
| 5,631,906 A | | 5/1997 | Liu et al. ..................... | 370/455 |
| 5,777,984 A | * | 7/1998 | Gun et al. ................... | 370/230 |
| 5,841,771 A | * | 11/1998 | Irwin et al. ................. | 370/360 |
| 5,867,480 A | * | 2/1999 | Thomas et al. ............. | 370/230 |
| 6,115,374 A | * | 9/2000 | Stonebridge et al. ....... | 370/362 |
| 6,147,969 A | * | 11/2000 | Benmohamed et al. ..... | 370/230 |
| 6,426,957 B1 | * | 7/2002 | Hauser et al. .............. | 370/413 |

FOREIGN PATENT DOCUMENTS

EP           676701 A1  *  10/1995   ........... G06F/13/28

OTHER PUBLICATIONS

The QPSX Man, Newman et al., IEEE Comm. Mag., Apr. 1988, pp. 20–28.
Improving the Fairness of Distributed–Queue–Dual–Bus Networks; Hahne et al., IEEE 1990, pp. 175–184.
ATM Ring Protocol and Performance, Ohnishi et al., IEEE 1989, pp. 394–398.

* cited by examiner

*Primary Examiner*—Hassan Kizou
*Assistant Examiner*—Dmitry Levitan
(74) *Attorney, Agent, or Firm*—Gordon & Jacobson, P.C.

(57) ABSTRACT

A multiport non-blocking high capacity ATM and packet switch is a single chip switching solution for ATM and packet systems. It is capable of 8×8 switching of 800 Mbit/s per port in both directions. The ports support UTOPIA Level 2 interfaces. The switch is non-blocking and lossless, incorporating a backpressure mechanism for eliminating congestion toward any one port. The switch supports prioritized and variable size cell and packet switching.

16 Claims, 6 Drawing Sheets

| BIT-7 | BIT-6 | BIT-5 | BIT-4 | BIT-3 | BIT-2 | BIT-1 | BIT-0 |
|---|---|---|---|---|---|---|---|
| PADDING (0/2/4/6/8/10 BYTES) ||||||||
| RESERVED | RESERVED | RESERVED | RESERVED | PORT 8 | PORT 7 | PORT 6 | PORT 5 |
| PORT 4 | PORT 3 | PORT 2 | PORT 1 ||||
| VCI ||||||||
| VCI ||||||||
| | | | | PT | | CLP |
| UDF-1 (HEC) ||||||||
| UDF-2 (SOURCE PORT ADDRESS) ||||||||
| ATM CELL PAYLOAD (48 BYTE) ||||||||

FIG.3

| BIT-7 | BIT-6 | BIT-5 | BIT-4 | BIT-3 | BIT-2 | BIT-1 | BIT-0 |
|---|---|---|---|---|---|---|---|
| RESERVED | RESERVED | RESERVED | RESERVED | PORT 8 | PORT 7 | PORT 6 | PORT 5 |
| PORT 4 | PORT 3 | PORT 2 | PORT 1 | | | | |
| PADDING (0/2/4/6/8/10/12 BYTES) | | | | | RESERVED | | |
| NON ATM PAYLOAD/PADDING | | | | | | | |

FIG.4

MULTIPORT NON-BLOCKING HIGH CAPACITY ATM AND PACKET SWITCH

BACKGROUND OF THE INVENTION

1. Field of the Invention

The invention relates to telecommunications. More particularly, the invention relates to a multiport non-blocking high capacity ATM and packet switch.

2. State of the Art

The first commercial digital voice communications system was installed in 1962 in Chicago, Ill. The system was called "T1" and was based on the time division multiplexing (TDM) of twenty-four telephone calls on two twisted wire pairs. The T1 system is still widely used today and forms a basic building block for higher capacity communication systems including T3 which transports twenty-eight T1 signals. The designations T1 and T3 were originally coined to describe a particular type of carrier equipment. Today T1 and T3 are often used to refer to a carrier system, a data rate, and various multiplexing and framing conventions. It is more accurate to use the designations "DS1" and "DS3" when referring to the multiplexed digital signal carried by the T1 and T3 carriers, respectively.

Today, another higher bandwidth TDM system is in use. This system is referred to as the synchronous optical network (SONET) or, in Europe, the synchronous digital hierarchy (SDH). The SONET network is designed to provide enormous bandwidth. SONET signals are referred to as Synchronous Transport Signals (STS) or Optical Carriers (OC). The narrowest SONET signal is referred to as STS-1 or OC-1. It has a bandwidth of 51.84 Mb/s which is sufficient to carry twenty-eight DS1 signals or a single DS3 signal. The hierarchy includes STS-3 (OC-3) which is three times the bandwidth of an STS-1 (OC-1) signal, and higher bandwidth signals increasing in multiples of four, i.e. STS-12 (OC-12), STS-48 (CC-48), STS-192 (OC-192), and STS-768 (OC-768).

The T1 and T3 networks were originally designed for digital voice communication. In a voice network minor bit errors can be tolerated as a small amount of noise. However, in a data network, a minor bit error cannot be tolerated. In the early 1970s, another technology was deployed to support data networks. The technology was called "packet switching". Unlike the T1 and T3 networks, packet switching was designed for data communications only. In packet switching, a "packet" of data includes a header, a payload, and a cyclic redundancy check (CRC). The header includes addressing information as well as an indication of the length of the payload. The payload contains the actual data which is being transmitted over the network. The CRC is used for error detection. The receiver of the packet performs a calculation with the bits in the packet and compares the result of the calculation to the CRC value. If the CRC value is not the same as the result of the calculation, it means that the packet was damaged in transit. According to the packet switching scheme, the damaged packet is discarded and the receiver sends a message to the transmitter to resend the packet. One popular packet switching scheme for wide area networks (WANs), known as X.25, utilizes a packet which has a fixed payload of 128 octets. Other packet switching schemes allow variable length packets up to 2,000 octets. Frame Relay is an example of a WAN packet switching scheme which utilizes variable sized packets and Ethernet is an example of a local area network (LAN) packet switching scheme which utilizes variable sized packets.

Concurrent with the development of packet switching several groups around the world began to consider standards for the interconnection of computer networks and coined the term "internetworking". The leading pioneers in internetworking were the founders of ARPANET (the Advanced Research Projects Network). ARPA, a U.S. Department of Defense organization, developed and implemented the transmission control protocol (TCP) and the internet protocol (IP). The TCP/IP code was dedicated to the public domain and was rapidly adopted by universities, private companies, and research centers around the world. An important feature of IP is that it allows fragmentation operations, i.e. the segmentation of packets into smaller units. This is essential to allow networks which utilize large packets to be coupled to networks which utilize smaller packets. Today, TCP/IP is the foundation of the Internet. It is used for email, file transfer, and for browsing the Worldwide Web. It is so popular that many organizations are hoping to make it the worldwide network for all types of communication, including voice and video.

Perhaps the most awaited, and now fastest growing technology in the field of telecommunications is known as Asynchronous Transfer Mode (ATM) technology. ATM was originally conceived as a carrier of integrated traffic, e.g. voice, data, and video. ATM utilizes fixed length packets (called "cells") of 53 octets (5 octets header and 48 octets payload). ATM may be implemented in either a LAN or a WAN.

Current ATM service is offered in different categories according to a user's needs. Some of these categories include constant bit rate (CBR), variable bit rate (VBR), unspecified bit rate (UBR), and available bit rate (ABR). CBR service is given a high priority and is used for streaming data such as voice and video where a loss of cells would cause a noticeable degradation of the stream. UBR and ABR services are given a low priority and are used for data transfers such as email, file transfer, and web browsing where sudden loss of bandwidth (bursty bandwidth) can be tolerated. ATM service is sometimes referred to as "statistical multiplexing" as it attempts to free up bandwidth which is not needed by an idle connection for use by another connection.

ATM switches (like other packet switches) typically include multiple buffers, queues, or FIFOs for managing the flow of ATM cells through the switch. Generally, a separate buffer is provided for each outlet from the switch. However, it is also known to have separate buffers at the inlets to the switch. Buffer thresholds are set to prevent buffer overflow. If the number of cells in a buffer exceeds the threshold, no more cells are allowed to enter the buffer. Cells attempting to enter a buffer which has reached its threshold will be discarded.

Within the ATM technology, a commonly used interface specification for passing ATM cells between chips on a circuit board is the UTOPIA interface. The UTOPIA interface is specified in ATM Forum standard specification af_phy_0039.000 (UTOPIA Level 2, Version 1, June 1995) which is hereby incorporated by reference herein in its entirety. The present UTOPIA standard defines an interface between a so-called PHY (physical) device and an ATM device for the transfer of fixed length ATM cells. According to the UTOPIA standard, the PHY device is responsible for performing cell-delineation (via the header error correction (HEC) code) and for (de)scrambling the cell payload of the ATM cells. The PHY device may also perform lower level framing functions, for example, SONET framing. The ATM device is responsible for higher level functions such as buffering and scheduling ATM cells and SAR.

Today, SONET, ATM, and IP are converging to provide consumers and businesses with multiple telecommunications services such as multimedia conferencing, video on demand, and high speed Internet access. Moreover, because of changes in the regulation of the telecommunications companies, many companies now compete to provide the same or similar services. Given the number of competing companies and the amount of bandwidth sought, an increasingly large number of physical switches are in use.

In order to lower the costs associated with providing telecommunications services, it is desirable to create broadband switching components which are smaller in size.

SUMMARY OF THE INVENTION

It is therefore an object of the invention to provide a high capacity switch on a single chip.

It is also an object of the invention to provide a high capacity switch on a single chip which has multiple UTOPIA Level 2 ports on the chip.

It is another object of the invention to provide a high capacity switch which is non-blocking.

It is still another object of the invention to provide a high capacity switch which incorporates a backpressure mechanism for eliminating congestion toward any port.

In accord with these objects which will be discussed in detail below, the switch according to the invention is a cell-based switch on a single chip having an internal unidirectional slotted looped bus, a bus controller, a microprocessor interface, and eight UTOPIA switch ports.

The bus controller performs several functions. It continuously generates fixed size time slots, or "free cells" to the bus, terminates received cells and relays undelivered cells to the bus. It provides a host microprocessor interface for switch management and controls cell access between the host and remote processors through one or multiple switch ports. It collects switch statistics and, together with each switch port, performs a medium access control protocol for prioritized fair cell access among all the switch ports.

The internal unidirectional slotted looped bus and the medium access control protocol are preferably based on co-owned U.S. Pat. Nos. 5,402,422 and 5,631,906, the complete disclosures of which are hereby incorporated herein by reference.

Each port includes a full duplex switch interface with two ingress FIFO buffers (high priority and low priority), five egress FIFO buffers (control, high priority multicast, low priority multicast, high priority unicast and low priority unicast), a flow control mechanism which includes a counter array and a backpressure indicator, as well as a 16-bit mode UTOPIA Level 2 compliant interface.

The internal cell size on the looped bus is 80 bytes. For each cell, the first 16 byte overhead is used for the MAC (Medium Access Control) field, address/map fields, and high-speed inter-block communication fields. The remaining 64 bytes are used to carry the payload. The switch is configurable to handle both ATM cells and non-ATM packets.

For unicast traffic, the flow control mechanism is per egress queue based. For multicast traffic, however, it is global. A centralized 32-bit backpressure bitmap located inside the bus controller provides congestion status from egress queues to each ingress port. For each priority level of multicast, a common UTOPIA port address is used for all ports and a common backpressure bit is used.

The two ingress FIFO buffers at each port store and forward cells coming from the UTOPIA Level 2 interface. To prevent egress queue overflow, a nineteen counter array is employed at the ingress port to count the number of cells destined for each egress queue from each of the ingress queues. There are sixteen counters for unicast traffic logging. In addition, there are three counters to count cells destined for the two multicast queues and the control traffic queue. When a cell arrives, regardless of which buffer it belongs to, a corresponding counter, identified by the cell destination queue address, is increased by 1. When a cell leaves either buffer, the same counter is decreased by 1. Thus, each counter records the number of cells outstanding in the ingress buffers for a particular egress queue. A back-pressure signal for each egress queue can be generated with respect to a predetermined counter threshold value. When a counter value reaches the threshold, that is, ingress congestion occurs, a backpressure signal is asserted to stop the UTOPIA Level 2 interface from accepting any further cells destined for that particular egress queue. When the counter value decreases from the threshold, the backpressure signal is immediately de-asserted so that other cells destined for that egress queue can be accepted.

According to the presently preferred embodiment, backpressure signals are asserted when either ingress or egress congestion occurs. Between the two back-pressure sources, a logical OR function is used for backpressure signal generation. In order to prevent head-of-line blocking, cells waiting in ingress buffers are switched regardless of backpressure bitmap changes.

Additional objects and advantages of the invention will become apparent to those skilled in the art upon reference to the detailed description taken in conjunction with the provided figures.

BRIEF DESCRIPTION OF THE DRAWINGS

FIG. 3 is a table illustrating the format of the internal cell structure of the switch when configured to carry ATM cells;

FIG. 4 is a table illustrating the format of the internal cell structure of the switch when configured to carry non-ATM packet payload;

DESCRIPTION OF THE APPENDIX

Attached hereto as an appendix is the Transwitch® TXC-05840 Data Sheet Product Preview (64 pages) which provides additional low level information about an embodiment of the invention which has been reduced to practice.

DETAILED DESCRIPTION OF THE PREFERRED EMBODIMENTS

Figure 1:
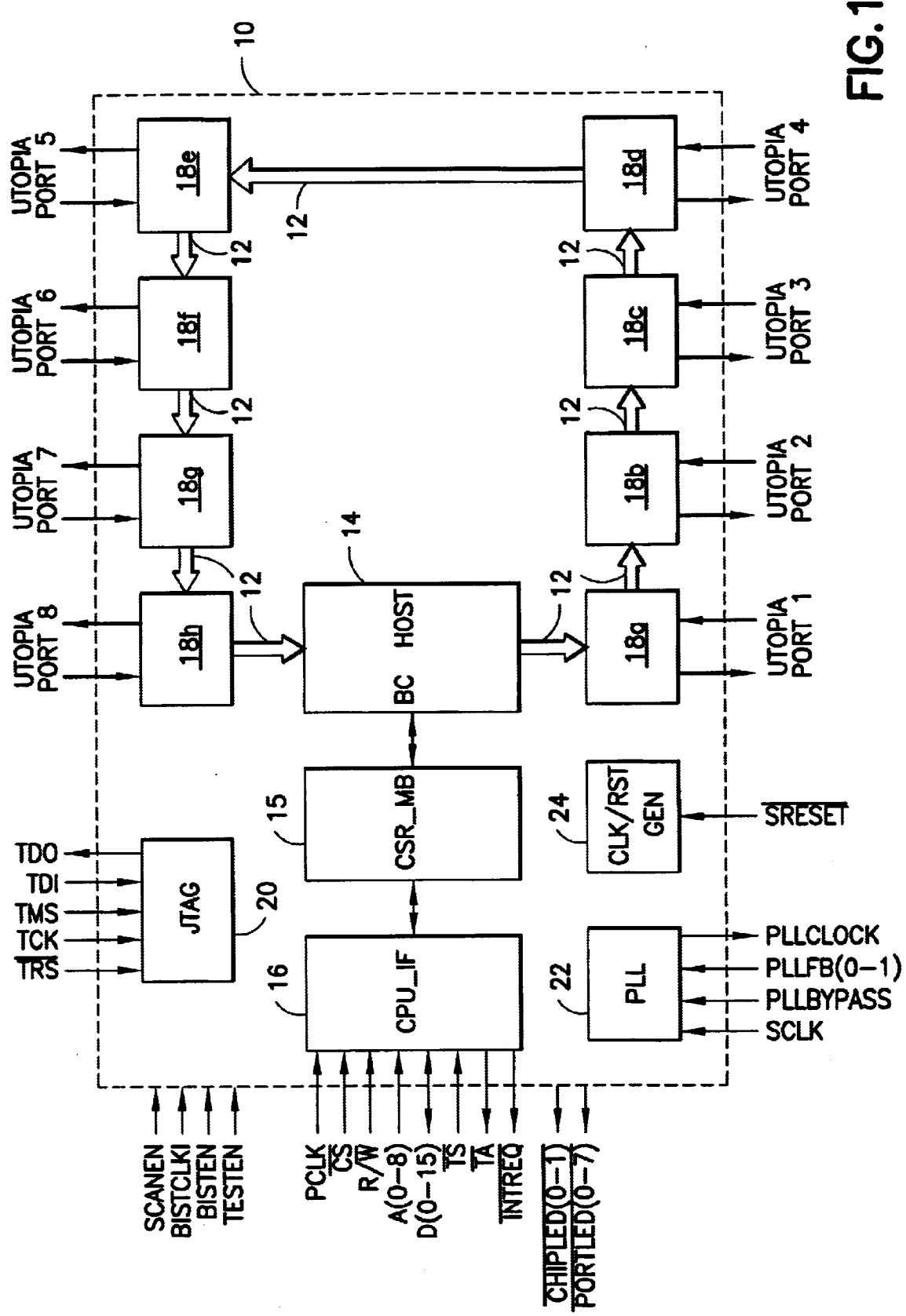
FIG. 1 is a high level block diagram of a switch according to the invention.

Referring now to FIG. 1, the switch 10 according to the invention is a cell-based switch on a single chip having an internal unidirectional slotted looped bus 12, a bus controller 14, a microprocessor interface 16, and eight switch ports 18a–18h. A ninth port is shown as part of the bus controller 14. As used herein, these ports may be referred to as ports 0–8. The bus controller 14 and the interface 16 are optionally coupled to a mailbox 15. The switch also includes an IEEE Joint Test Action Group (JTAG) interface 20, a phase locked loop (PLL) 22, and a resettable clock generator 24.

According to the presently preferred embodiment, the bus 12 is 128-bits (sixteen bytes) wide and is clocked at 200 MHz. The internal cell size on the bus is eighty bytes. Thus, a cell is moved onto or off of the bus in five clock cycles. For each cell, the first sixteen bytes are overhead used for the MAC (Medium Access Control) field, address/map fields, and high-speed inter-block communication fields. The remaining sixty-four bytes are used to carry the payload. The switch is configurable to handle both ATM cells and non-ATM packets as discussed below with reference to FIGS. 3 and 4.

The bus controller 14 performs several functions. It continuously generates fixed size time slots, or "free cells" to the bus 12, terminates received cells and relays undelivered cells to the bus 12. It provides a host microprocessor interface for switch management and control cell access between the host and remote processors through one or multiple switch ports. It collects switch statistics and, together with each switch port 18a–18h, performs a medium access control protocol for prioritized fair cell access among all the switch ports.

The signals SCANEN, BISTCLKI, BISTEN, and TESTEN are provided for testing. SCANEN is scan enable and is an internal test function. TESTEN is scan test enable, used for factory testing. BSTCLKI is an internal memory BIST clock. BISTEN is internal memory BIST enable.

Figure 2:
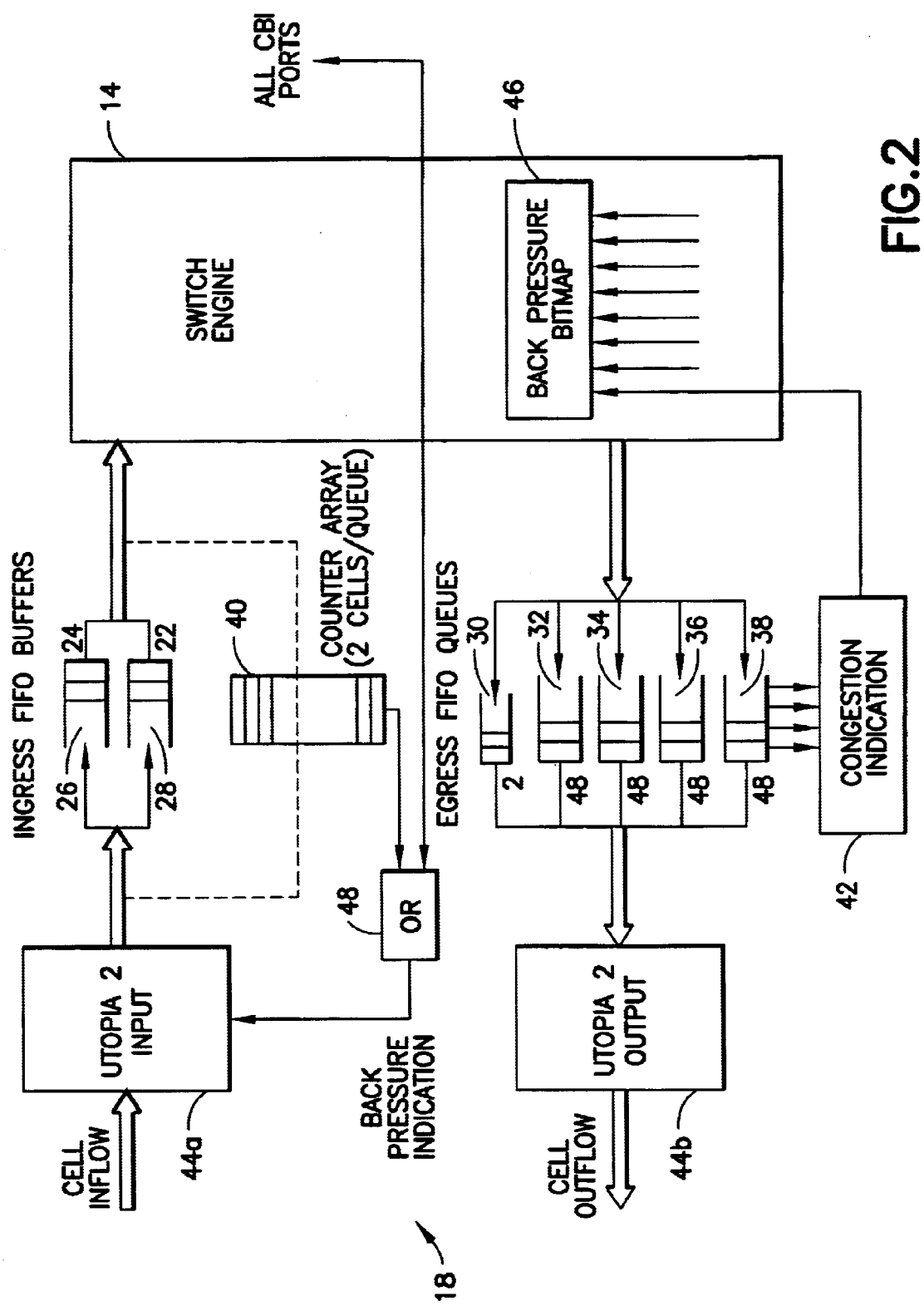
FIG. 2 is a high level block diagram of one of the ports of the switch.

Turning now to FIG. 2, each port 18a–18h includes a full duplex switch port interface with a high priority ingress FIFO buffer 26, a low priority ingress FIFO buffer 28, a control egress FIFO buffer 30, a high priority multicast egress FIFO buffer 32, a low priority multicast egress FIFO buffer 34, a high priority unicast egress FIFO buffer 36, and a low priority unicast egress FIFO buffer 38. Each port also includes a flow control mechanism which includes a counter array 40 and a backpressure indicator 42. Each port also includes a sixteen-bit mode UTOPIA Level 2 compliant interface 44a, 44b.

FIG. 3 illustrates the cell structure when the switch is configured to carry ATM cells. In ATM mode, the cell can be 54/56/58/60/62/64 bytes, corresponding to the padding of 0/2/4/6/8/10 bytes. The last fifty-four bytes are used for carrying a standard ATM cell and a multicast bitmap. As shown in FIG. 3, the first twelve bits of the ATM cell (VPI field for the NNI cell structure) is used to carry the multicast bitmap. Since the present implementation of the switch has eight ports, four of the twelve bits are not used but are reserved. The UDF2 field of the ATM cell is used to carry the source port address.

FIG. 4 illustrates the cell structure for non-standard ATM or packet cells. As shown in FIG. 4, the multicast bitmap can be placed anywhere within the first fourteen bytes of the cell. During the switch initialization, a three-bit field of enable switch command (EN_SW) is used to specify the start byte of this multicast bitmap. The valid start byte position is from byte 1 to byte 13. All the other bytes not used for the multicast bitmap can be used for carrying overhead or payload.

Referring once again to FIG. 2, for unicast traffic, the flow control mechanism is egress queue based. For multicast traffic, however, it is global. A centralized thirty-two-bit backpressure bitmap 46 located inside the switch engine 14 provides congestion status from egress queues 30, 32, 34, 36, 38 to each ingress port 44a. For each priority level of multicast, a common UTOPIA port address is used for all ports and a common backpressure bit is used. According to the presently preferred embodiment, UTOPIA PHY addresses are mapped to port egress queues as shown in Table 1.

TABLE 1

| UTOPIA PHY Address | Egress Queue | Port Number |
|---|---|---|
| 0 | Control | 0 |
| 1 | Multicast High Priority | 1–8 |
| 2 | Multicast Low Priority | 1–8 |
| 3 | Unicast High Priority | 1 |
| 4 | Unicast Low Priority | 1 |

TABLE 1-continued

| UTOPIA PHY Address | Egress Queue | Port Number |
|---|---|---|
| 5 | Unicast High Priority | 2 |
| 6 | Unicast Low Priority | 2 |
| 7 | Unicast High Priority | 3 |
| 8 | Unicast Low Priority | 3 |
| 9 | Unicast High Priority | 4 |
| 10 | Unicast Low Priority | 4 |
| 11 | Unicast High Priority | 5 |
| 12 | Unicast Low Priority | 5 |
| 13 | Unicast High Priority | 6 |
| 14 | Unicast Low Priority | 6 |
| 15 | Unicast High Priority | 7 |
| 16 | Unicast Low Priority | 7 |
| 17 | Unicast High Priority | 8 |
| 18 | Unicast Low Priority | 8 |
| 19–31 | Reserved | Reserved |

Of the five egress queues 30, 32, 34, 36, 38, four are dedicated to user traffic and one is for control traffic. The descending order of priority is control traffic, high priority multicast, high priority unicast, low priority multicast, and low priority unicast. The user traffic buffers are all the same length, e.g. forty-eight cells as shown in FIG. 2. The control queue does not require so large a buffer. As shown in FIG. 2, a two cell buffer is sufficient for control traffic.

The two ingress FIFO buffers 26, 28 at each port store and forward cells coming from the UTOPIA Level 2 interface 44a. To prevent egress queue overflow, an array of nineteen counters 40 is employed to count the number of cells destined for each egress queue from each of the ingress queues. There are sixteen counters for unicast traffic logging. In addition, there are three counters to count cells destined for the two multicast queues and the control traffic queue. When a cell arrives, regardless of which buffer in which port it belongs to, a corresponding counter, identified by the cell destination queue address, is increased by 1. When the cell leaves the queue, the same counter is decreased by 1. Thus, each counter records the number of cells outstanding in the ingress buffers for each egress queue in the switch. A backpressure signal for each egress queue can be generated from the nineteen counter array with respect to predetermined counter threshold values. When a counter value reaches the threshold, a backpressure signal is asserted to stop the UTOPIA Level 2 interface 44a from accepting any further cells destined for that particular egress queue. When the counter value decreases from the threshold, the backpressure signal is immediately de-asserted so that other cells destined for that egress queue can be accepted.

According to the presently preferred embodiment, each of the ingress buffers are permitted to hold up to two cells for the same egress queue. Thus, each counter of the counter array 40 counts up to two cells for each egress queue destination. For a switch with N ports, the high priority ingress queue of each port should therefore hold 2*(N+2) cells and the low priority queue should hold 2*(N+1) cells. Although the presently preferred embodiment of the switch has eight ports, the buffer sizes indicated in FIG. 2 are for a ten-port switch.

Unlike ingress flow control, egress backpressure is controlled globally. To perform lossless cell switching between multiple ports and to support heterogeneous port speed switch configurations, each egress user traffic queue must be able to absorb burst traffic simultaneously coming from multiple ingress ports for a certain time period. When an egress queue accumulates cells up to a point possibly causing overflow, it raises a warning signal and the signal sets a relative bit in the backpressure bitmap. Through a feedback mechanism, this will immediately trigger all ingress ports to stop accepting any more cells destined for the congested egress queue. Two parameters are used to determine when to raise and lower the warning signal. These are high watermark adjustment (HWMA) and watermark offset (WM_OFFSET). HWMA is used for raising the congestion condition flag and WM_OFFSET is used for clearing the congestion condition flag. Both parameters are user programmable. The parameter HWMA is switch based and it is set globally. The parameter WM_OFFSET is per port based and it is set individually. Users can change each parameter dynamically to optimize applications performance in terms of active port numbers and port rate. When the cell inflow rate is greater than the cell outflow rate in an egress queue, cells will accumulate in the queue. When the number of cells reaches the predetermined HWMA point, a congestion condition is indicated and a corresponding bit in the backpressure bitmap is set.

At any given moment, there can be multiple cells in transition on the switch bus. The number of cells in transition depends on the number of switch ports. For the worst case scenario, all the cells in transition may destined for a congested egress queue. Moreover, each ingress port can hold up to two cells destined for the same egress queue. To prevent cell overflow for such a case, the HWMA value must be greater or equal to the maximum number of cells in transition plus two cells coming from each of the active ingress queues. The value of HWMA can be expressed as Equation (1) where $C_t$ and $P_{active}$ denote cells in transition and number of active ingress ports, respectively.

$$HWMA \geq C_t + 2(P_{active} - 1) \quad (1)$$

When the number of cells in a queue drops to a congestion clearance point, the congestion flag is lowered. The congestion clearance point is defined as the queue size less the HWMA less the WM_OFFSET. For a Utopia2 interface rate, the minimum congestion clearance point is 2. For higher speed port rate, the congestion clearance point must be larger, e.g. between 4 and 8. In switches with heterogeneous port speeds, each port may keep separate WM_OFFSET value.

According to the preferred embodiment, backpressure signals are asserted when either ingress or egress congestion occurs. Between the two backpressure sources, a logical OR function 48 is used for backpressure signal generation to the UTOPIA input interface 44a. In order to prevent head-of-line blocking, cells waiting in ingress queues 26, 28 are switched regardless of backpressure bitmap changes.

When the UTOPIA input interface receives a backpressure indication, it uses standard UTOPIA signaling to refuse cells destined for the affected queue.

It will be appreciated that in the case of multicast cells, congestion at any one egress queue will cause a backpressure indication at the source port which will affect all destination ports. To alleviate this outcome, an egress link status based timeout mechanism is available to prevent multicast backpressure from starving multicast traffic for an excessive time due to link failure experienced at an egress port. The timeout mechanism utilizes a timer (not shown) to monitor the egress link status. A transmission of any cell from the egress port resets the timer. The timer is started when any egress queue is not empty and the transmission does not occur. A link failure is detected when the timer expires. In that case, the affected port cancels both multicast backpressures regardless of congestion status. As a result, a link failure at one egress port will not affect multicast cell deliveries of the other egress ports. The egress port experiencing link failure will eventually drop all cells due to queue overflow.

Whenever a link failure is detected, the affected egress port generates an interrupt to the host (if not masked). The host is able to monitor relative statistics counters of user traffic to determine whether a link failure is recovered. The host can also issue control cells to test the condition of the egress port link status by checking the value change of the egress control counter. The link status recovery is triggered by the transmission of either a unicast or a multicast cell. Upon such an instance, the affected egress port resets the timeout timer and restores normal operation of the multicast backpressure mechanism.

The timeout value is determined during the switch initialization. The default value can be 1 or 2 ms. For any ports not activated, cells coming to them from the switch bus are always dropped.

Figure 5:
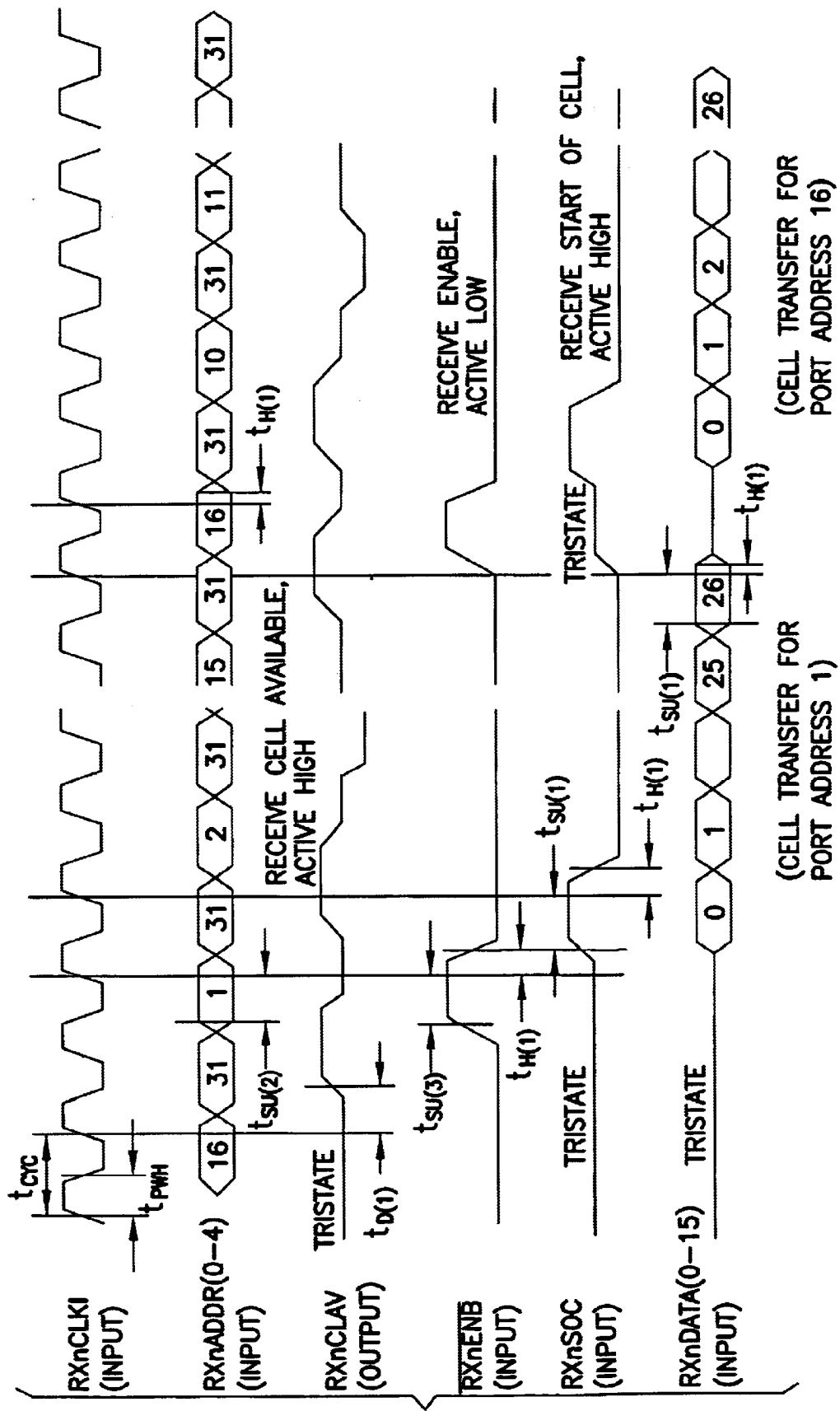
FIG. 5 is a timing diagram illustrating the timing of UTOPIA transmit Multi-PHY.
Figure 6:
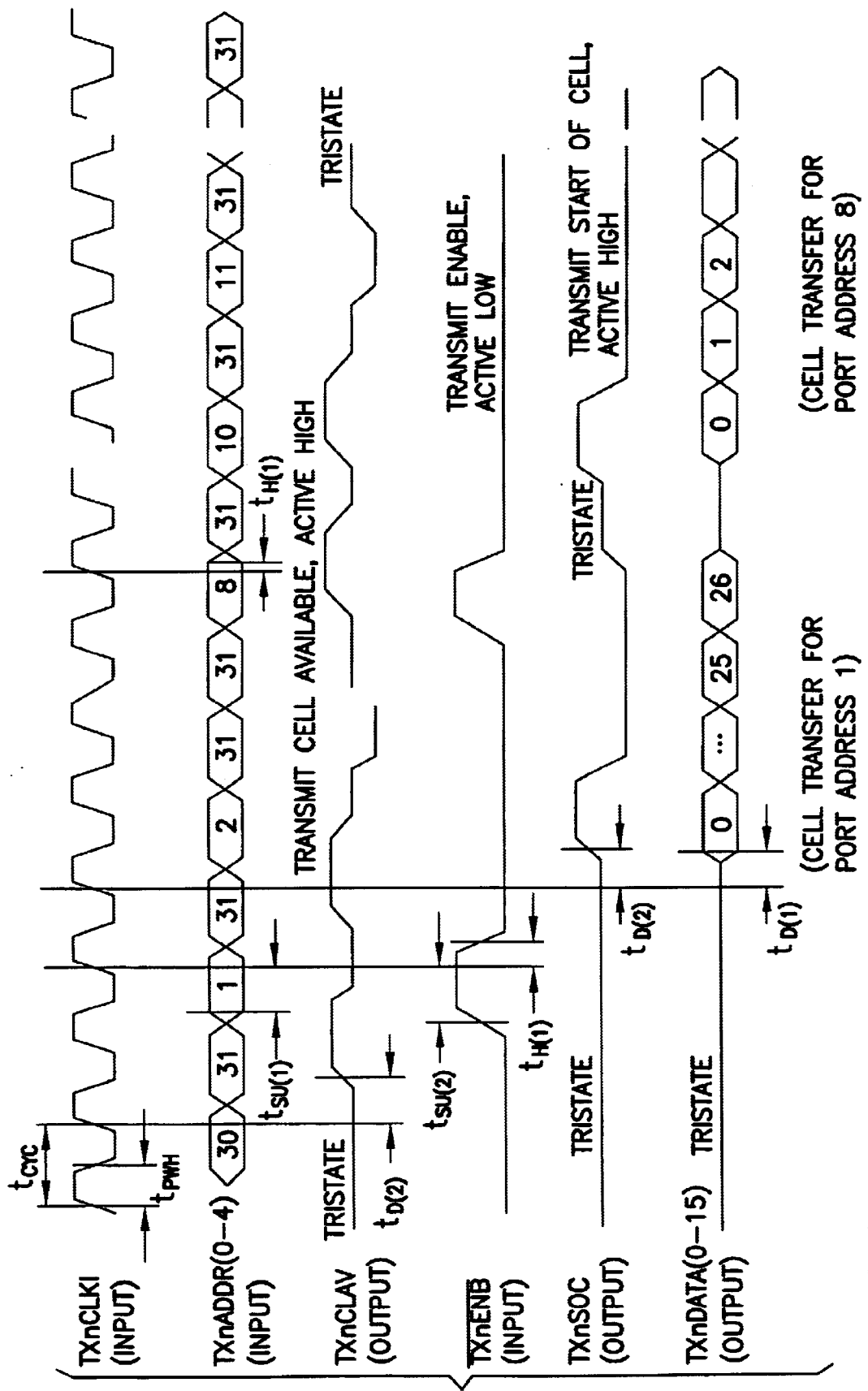
FIG. 6 is a timing diagram illustrating the timing of UTOPIA receive Multi-PHY.

Detailed timing diagrams for the UTOPIA interfaces of the switch are provided in FIGS. 5 and 6, with values for the timing intervals given in Tables 2 and 3. All output times are measured with a maximum 25 pF load capacitance, unless noted otherwise. Timing parameters are measured at voltage levels of $(V_{IH}+V_{IL})/2$ and $(V_{OH}+V_{OL})/2$, for input and output signals, respectively.

As used herein, RXnCLKI is the port n egress terminal UTOPIA clock; RXnDATA is the port n egress terminal data; RXnSOC is the port n egress terminal start of cell; RXnADDR is the port n egress terminal address; RXnENB is the port n egress terminal enable; and RXnCLAV is the port n egress terminal cell available. Similarly, TXnCLKI is the port n ingress terminal UTOPIA clock; TXnADDR is the port n ingress terminal address; TXnENB is the port n ingress terminal enable; TXnDATA is the port n ingress terminal data; TXnSOC is the port n ingress terminal start of cell; and TXnCLAV is the port n ingress terminal cell available.

TABLE 2

| Parameter | Symbol | Min | Typ | Max | Unit |
|---|---|---|---|---|---|
| RXnCLKI clock cycle time | $t_{CYC}$ | 20 | | | ns |
| RXnCLKI duty cycle, $t_{PWH}/t_{CYC}$ | | 40 | | 60 | % |
| RXnDATA (0–15), RXnSOC setuptime to RXnCLKI | $t_{SU(1)}$ | 4.0 | | | ns |
| RXnADDR (0–4) setup time to RXnCLKI | $t_{SU(2)}$ | 5.0 | | | ns |
| RXnENB setup time to RXnCLKI | $t_{SU(3)}$ | 6.0 | | | ns |
| RXnDATA (0–15), RXnSOC, RXnADDR (0–4), RXnENB hold time after RXnCLKI | $t_{H(1)}$ | 1.0 | | | ns |
| RXnCLAV delay from RXnCLKI | $t_{D(1)}$ | 2.0 | | 12 | ns |

TABLE 3

| Parameter | Symbol | Min | Typ | Max | Unit |
|---|---|---|---|---|---|
| TXnCLKI clock cycle time | $t_{CYC}$ | 20 | | | ns |
| TXnCLKI duty cycle, $t_{PWH}/t_{CYC}$ | | 40 | | 60 | % |
| TXnADDR (0–4) setuptime to TXnCLKI | $t_{SU(1)}$ | 4.0 | | | ns |
| TXnENB setup time to RXnCLKI | $t_{SU(2)}$ | 7.5 | | | ns |
| TXnENB, TXnADDR (0–4) HOLD time after TXnCLKI | $t_{H(1)}$ | 1.0 | | | ns |
| TXnDATA (0–15) delay from TXnCLKI | $t_{D(1)}$ | 2.0 | | 11.5 | ns |
| TXnSOC, TXnCLAV delay from TXnCLKI | $t_{D(2)}$ | 2.0 | | 11 | ns |

There have been described and illustrated herein a multiport non-blocking high capacity atm and packet switch. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as so claimed.

(Fold back on this line second, then tape closed, stamp and mail.)

TRANSWITCH
3 Enterprise Drive
Shelton, CT 06484-4694
U.S.A.

First
Class
Postage
Required

TranSwitch Corporation
Attention: Marketing Communications Dept.
3 Enterprise Drive
Shelton, CT 06484-4694
U.S.A.

(Fold back on this line first.)

Please complete the registration form on this back cover sheet, and fax or mail it, if you wish to receive updated documentation on this TranSwitch product as it becomes available.

---

TranSwitch Corporation • 3 Enterprise Drive • Shelton, CT 06484 USA • Tel: 203-929-8810 • Fax: 203-926-9453 • www.transwitch.com

AsTriX™ Device
*CellBus®* Expansion Switch
TXC-05840

DATA SHEET
*PRODUCT PREVIEW*

FEATURES

- Interoperable with CUBIT®-3 (TXC-05804), CUBIT-622 (TXC-05805), Sertopia™ (TXC-05860), and ASPEN® (TXC-05810) UTOPIA Level 2 interface
- Non-blocking switching capacity
- 8 UTOPIA Level 2 ports (800 Mbit/s per port)
- Configurable cell (or packet chunk) size per port of 52 to 64 bytes
- Host insertion/extraction for the local host interface
- 16-bit general purpose microprocessor interface
- Motorola MPC850/860 microprocessor compatible
- Backpressure mechanism to avoid cell loss
- Two priority levels supported for both unicast and multicast to any combination of destination ports
- Future OC-48 expansion capability
- Operation with a single 50 MHz clock
- Per port statistics supported
- Chip diagnostic mode supported
- Built in self test for power-on reset
- LED leads for chip status and port status
- Test Access Port for IEEE 1149.1 boundary scan
- +3.3 V and +1.8 V power supplies
- 640-lead Plastic Ball Grid Array package (PBGA), 31 mm x 31 mm

DESCRIPTION

The AsTriX™ (TXC-05840) *CellBus* expansion switch is a single chip switching solution for ATM systems. In order to meet the accelerating need for bandwidth in access systems, the AsTriX is designed to allow higher *CellBus* system throughput by concatenating multiple *CellBus* strands through a switch. It is capable of 8 x 8 switching of 800 Mbit/s per port. The AsTriX ports support UTOPIA Level 2 interfaces. The switch is non-blocking, incorporating a backpressure mechanism for eliminating congestion towards any one port.

The switch may be used to scale a *CellBus* architecture to deliver up to 9.6 Gbit/s system bandwidth, by connecting up to 8 *CellBus* segments (each capable of 1.2 Gbit/s switching). A single port (or multiple ports) may be used to implement an OC-12 uplink in a mux application.

Together with TranSwitch's CUBIT, ASPEN and Sertopia family devices, the AsTriX switch device can be used to create a cost effective point-to-point serial backplane based access system. With two switch devices operating in tandem, the system bandwidth can scale up to 19.2 Gbit/s.

APPLICATIONS

- Remote Access Concentrators
- Multi-service Access Devices
- Digital Cross Connect Systems
- DSLAM
- Routers

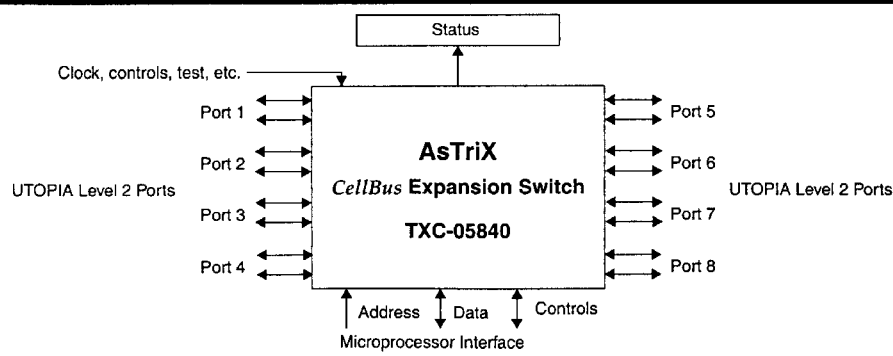

Copyright © 2001 TranSwitch Corporation
AsTriX and Sertopia are trademarks of TranSwitch Corporation
TranSwitch, TXC, ASPEN, CUBIT and CellBus are registered trademarks of TranSwitch Corporation Document Number:
*PRODUCT PREVIEW* TXC-05840-MB
Ed. 1, July 2001

TranSwitch Corporation • 3 Enterprise Drive • Shelton, Connecticut 06484 • USA
Tel: 203-929-8810 • Fax: 203-926-9453 • www.transwitch.com Proprietary TranSwitch Corporation Information for use Solely by its Customers

**AsTriX
TXC-05840        DATA SHEET        TRANSWITCH®**

TABLE OF CONTENTS

| Section | Page |
| --- | --- |
| List of Figures | 3 |
| Block Diagram | 4 |
| Block Diagram Description | 4 |
| Operation | 8 |
|     Cell Structure | 8 |
|     Prioritized Cell Switching | 9 |
|     Switch Medium Access Control (MAC) | 9 |
|     Unicast and Multicast Cell Delivery | 10 |
|     CBI (CellBus Interface) Port | 11 |
|         Ingress Buffering | 11 |
|         Egress Queueing | 11 |
|         UTOPIA Level 2 Interface | 12 |
|         Address Conversion | 12 |
|         Flow Control | 13 |
|         Ingress Flow Control | 13 |
|         Egress Flow Control | 13 |
|         Egress Queue Timeout Mechanism for Multicast Traffic | 14 |
|     Statistics Collection | 15 |
|         Switch Based Statistics | 15 |
|         CBI Port Based Statistics | 16 |
|     Operation Modes | 17 |
|         Reset Mode | 17 |
|         Initialization Mode | 17 |
|         Normal Mode | 17 |
|         Diagnostic Mode | 18 |
|     Microprocessor Interface and Mailboxes | 19 |
|     Boundary Scan | 20 |
| Lead Descriptions | 22 |
| Absolute Maximum Ratings and Environmental Limitations | 29 |
| Thermal Characteristics | 29 |
| Power Requirements | 29 |
| Input, Output and Input/Output Parameters | 30 |
| Timing Characteristics | 32 |
| Register Definition and Host Access | 38 |
|     General Access Scheme | 38 |
|     Register Description | 38 |
|     Register Mapping | 49 |
|     Mailbox Content Page | 51 |
| Package Information | 54 |
| Ordering Information | 55 |
| Related Products | 55 |
| Application Examples | 56 |
| Reference Documents | 57 |
| Standards Documentation Sources | 58 |
| Documentation Update Registration Form* | 63 |

\* Please note that TranSwitch provides documentation for all of its products. Current editions of many documents are available from the Products page of the TranSwitch Web site at www.transwitch.com. Customers who are using a TranSwitch Product, or planning to do so, should register with the TranSwitch Marketing Department to receive relevant updated and supplemental documentation as it is issued. They should also contact the Applications Engineering Department to ensure that they are provided with the latest available information about the product, especially before undertaking development of new designs incorporating the product.

Proprietary TranSwitch Corporation Information for use Solely by its Customers

TranSwitch® DATA SHEET — AsTriX TXC-05840

LIST OF FIGURES

| Figure | | Page |
|---|---|---|
| 1 | AsTriX (TXC-05840) Block Diagram | 4 |
| 2 | CBI Port Structure | 5 |
| 3 | AsTriX Operation Modes | 7 |
| 4 | AsTriX Cell Structure | 8 |
| 5 | AsTriX ATM Cell Structure | 8 |
| 6 | AsTriX Non-Standard ATM Cell Structure | 9 |
| 7 | AsTriX Priority Mapping | 9 |
| 8 | MC_Bitmap Field for Multicast Cell Delivery | 10 |
| 9 | Address Mapping | 12 |
| 10 | Egress Queue Based Flow Control | 13 |
| 11 | Boundary Scan Top-Level Block Diagram | 21 |
| 12 | Timing of UTOPIA Transmit Multi-PHY (PHY Layer Emulation) (16-bit) | 32 |
| 13 | Timing of UTOPIA Receive Multi-PHY (PHY Layer Emulation) (16-bit) | 33 |
| 14 | Motorola Microprocessor Read Cycle Timing | 34 |
| 15 | Motorola Microprocessor Write Cycle Timing | 35 |
| 16 | Microprocessor Interrupt Timing | 36 |
| 17 | Boundary Scan Timing | 37 |
| 18 | AsTriX TXC-05840 640-Lead Plastic Ball Grid Array Package | 54 |
| 19 | CellBus Shelf Aggregation Application Using the AsTriX TXC-05840 | 56 |

*PRODUCT PREVIEW*

BLOCK DIAGRAM

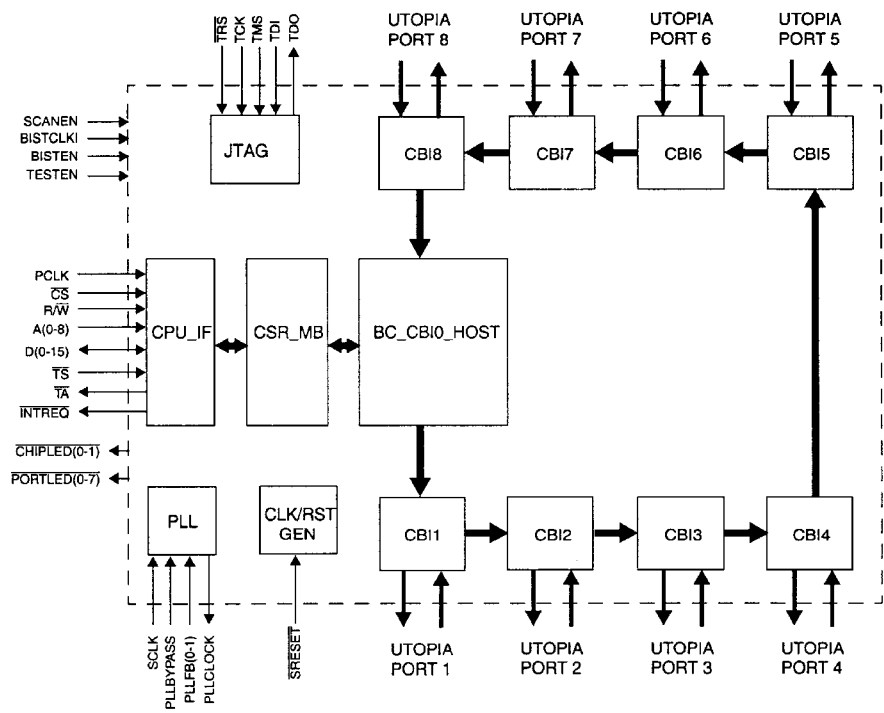

Figure 1. AsTriX (TXC-05840) Block Diagram

BLOCK DIAGRAM DESCRIPTION

A block diagram of the AsTriX device is shown in Figure 1. Further information on device operation and the interfaces to external circuits is provided below in the following Operation section.

The AsTriX *CellBus* Expansion Switch device is a cell-based switch, consisting of an internal unidirectional slotted looped bus, a bus controller, a microprocessor interface, and eight UTOPIA Level 2 interface compatible switch ports. There are a total of eight switch ports, CBI1 - CBI8. Each CBI (*CellBus* Interface) port interface is UTOPIA Level 2 compliant. CBI0 is a special purpose switch port existing inside the bus controller for control cell access between a microprocessor host and the switch.

Proprietary Switch Corporation Information for use Sol / its Customers

TranSWITCH           DATA SHEET          AsTriX TXC-05840

The bus controller performs several functions: 1) it continuously generates fixed size time slots, or free cells to the bus; 2) it terminates received cells and relays undelivered cells to the bus; 3) it provides a host microprocessor interface for switch management and control cell access between the host and remote processors through one or multiple CBI switch ports; 4) it collects switch statistics; and 5) it, together with each CBI port, performs a medium access control protocol for prioritized fair cell access between all the CBI switch ports.

CBI (CellBus INTERFACE) PORT

A CBI port is a full duplex switch port consisting of the following elements: 2 ingress FIFO buffers (high-priority and low-priority), full duplex switch engine access, 5 egress FIFO queues, a flow control mechanism consisting of a counter array and a backpressure indication, as well as a 16-bit mode UTOPIA Level 2 compliant interface. Figure 2 below provides an overall CBI block diagram from an architectural viewpoint.

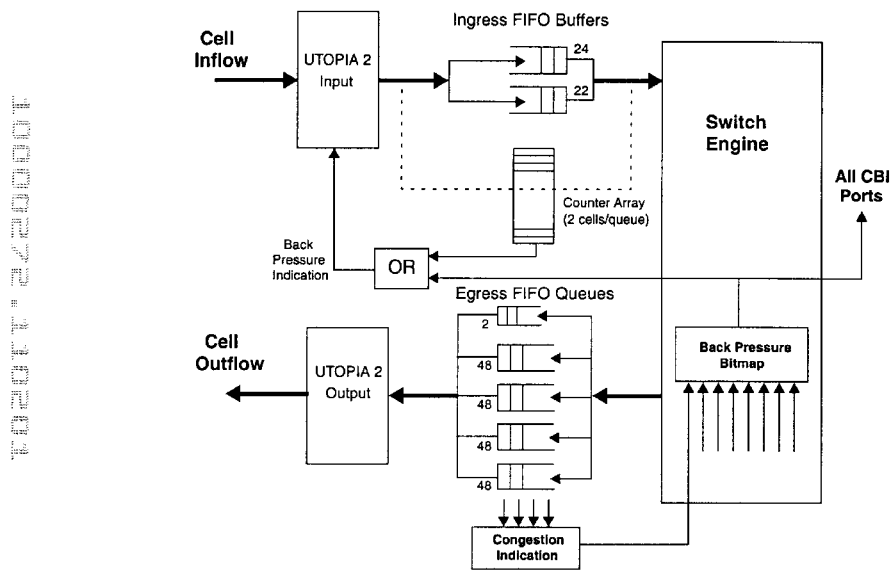

Figure 2. CBI Port Structure

All the CBI switch ports are homogeneous. Each CBI port provides an 800 Mbit/s information rate for full duplex cell transmission and reception.

The AsTriX provides prioritized cell switching. It supports high and low priorities for multicast cell switching, high and low priorities for unicast cell switching, and control cell switching. The cell switching priority sequence is control, high priority multicast, high priority unicast, low priority multicast and low priority unicast, in descending order. Each CBI has 5 egress FIFO queues, with one queue for each class of traffic.

The AsTriX includes a 16-bit microprocessor interface defined as CBI0. CBI0 is a special port for switch access by the host. The sole traffic type passing through this port is called control traffic which is always switched through high priority cell delivery. Logically, CBI0 is the first switch bus interface from the bus controller in the bus direction.

Proprietary Switch Corporation Information for use Sol its Customers

AsTriX
TXC-05840     DATA SHEET     TRANSWITCH

CELL STRUCTURE

The internal cell size on the looped bus is 80 bytes. For each cell, the first 16-byte overhead is used for MAC (Medium Access Control) field, address/map fields, and high-speed inter-block communication fields. And the last 64-byte is used to carry the payload.

The switch handles two types of cells, ATM and non-ATM (for packet). During switch initialization, the switch mode, ATM or non-ATM, is selected by the configuration register setting. The cell structures in ATM mode are different from those of non-ATM mode. In ATM mode, the source CBI port address needs to be inserted into the UDF field of each ATM cell by ingress CBI ports. In non-ATM mode, there is no such address insertion.

PRIORITIZED CELL SWITCHING

A two-level prioritized bus access scheme is used for cell switching between all the participating CBIs. Control traffic, high priority multicast, and high priority unicast all utilize high priority bus access to transfer cells and the rest utilize low priority for bus access. With this arrangement, even when the switch is overloaded, high priority traffic is guaranteed for bus access.

SWITCH MEDIUM ACCESS CONTROL (MAC)

The switch employs a MAC protocol that allows all the switch ports access to the bus for cell switching. The MAC protocol is designed for two-level prioritized asynchronous cell switching. Each CBI port utilizes two FIFO buffers to store cells coming from the UTOPIA Level 2 interface. Bus arbitration protocol provides a fair and efficient bus access among all ports through a bus reservation mechanism.

UNICAST AND MULTICAST CELL DELIVERY

The switch supports both unicast and multicast cell deliveries. Unicast is performed via point-to-point cell delivery, a source CBI transfers a cell to a destination CBI. The source CBI is responsible for filling the destination address field based on the destination address polled by an external UTOPIA Level 2 device. Two separate port/queues are reserved for multicast, representing high and low priority. The CBI destination for each multicast session is coded in the lower 8 bits of the VPI field (note: the cell header is retranslated by the receiving CUBIT-3 or ASPEN device).

STATISTICS COLLECTION

There are two types of statistics collected, switch based statistics and per-CBI port based statistics. A counter is used for each statistic. To prevent any counter overflow, the host periodically reads all the statistics counters. When a counter reaches half full, i.e., the most significant bit changes from 0 to 1, it generates an interrupt to the host. The host may mask such interrupts to avoid excessive interrupt processing.

Proprietary Switch Corporation Information for use Sol / its Customers

TranSwitch®  DATA SHEET

AsTriX
TXC-05840

OPERATION MODES

The AsTriX has four operation modes: the Reset Mode (RST_MODE), Initialization Mode (INIT_MODE), Normal Mode (NORMAL_MODE), and Diagnostic Mode (DIAG_MODE), as illustrated in Figure 3. Switch operation will be changed from one mode to the other upon issuance of the appropriate command by the local host.

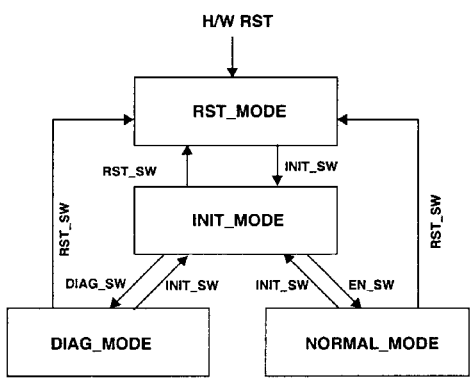

Figure 3. AsTriX Operation Modes

Details can be found in the operation mode description.

OTHER INTERFACES

Microprocessor Interface

The AsTriX *CellBus* Expansion Switch device integrates a 16-bit host microprocessor interface for transferring data and control information. This interface is Motorola MPC850/860 microprocessor compatible. The interface byte-lane model is Big Endian. This interface permits a host processor to configure the AsTriX *CellBus* Expansion Switch device and obtain statistics from the bus controller, and from each CBI port. Management traffic is also inserted and extracted by the host through this interface to communicate with remote processors connected to CUBIT-3 (TXC-05804), CUBIT-622 (TXC-05805), ASPEN (TXC-05810) or other devices.

Boundary Scan (Test Access) Port

The test interface includes a five-lead Test Access Port (TAP) as the boundary scan port that conforms to the IEEE 1149.1 standard. This standard provides external boundary scan functions to read and write the external input/output leads from the TAP for board and component test.

Proprietary Switch Corporation Information for use Sol / its Customers

AsTriX
TXC-05840     DATA SHEET     TRANSWITCH®

OPERATION

CELL STRUCTURE

Figure 4 shows the internal cell structure used in AsTriX. For each cell, the first 16-byte overhead is used for MAC (Medium Access Control) field, address/map fields, and high-speed inter-block communication fields. And the last 64-byte is used to carry the payload.

| Bytes | Field |
|---|---|
| 16 | Overhead |
| 64 | Payload |

Figure 4. AsTriX Cell Structure

The switch handles two types of cells, ATM and non-ATM, or packet. During switch initialization, the switch mode, ATM or non-ATM is selected by the configuration register setting. The cell structures in ATM mode are different from that of non-ATM mode. In ATM mode, the source CBI port address needs to be inserted into the UDF field of each ATM cell by egress CBI Ports. In non-ATM mode, there is no such address insertion.

Figure 5 shows the standard ATM cell structure as carried in the switch. For ATM mode, the cell can be 54/56/58/60/62/64 bytes, corresponding to the padding of 0/2/4/6/8/10 bytes. The last 54 bytes on each payload are used for carrying a standard ATM cell. In this case, the first 12 bits of the payload (VPI field for the NNI cell structure) is used for carrying the multicast bitmap. The UDF2 field are used to carry the source CBI port address by ingress CBI ports.

| Bit-7 | Bit-6 | Bit-5 | Bit-4 | Bit-3 | Bit-2 | Bit-1 | Bit-0 |
|---|---|---|---|---|---|---|---|
| Padding (0/2/4/6/8/10 bytes) ||||||||
| Reserved | Reserved | Reserved | Reserved | CBI8 | CBI7 | CBI6 | CBI5 |
| CBI4 | CBI3 | CBI2 | CBI1 | VCI ||||
| VCI ||||||||
| VCI |||||| PT | CLP |
| UDF1 (HEC) ||||||||
| UDF2 (Source CBI Port Address) ||||||||
| ATM Cell Payload (48 byte) ||||||||

Figure 5. AsTriX ATM Cell Structure

For non standard ATM, or packet cells, as shown in Figure 6, the multicast bitmap can be placed anywhere within the first 14 bytes of all the cells. During the switch initialization, a 3 bit field of enable switch command (EN_SW) is used to specify the start byte of this multicast bitmap. The valid start byte position is from byte 1 to byte 13. All the other bytes not used for the multicast bitmap can be used for carrying overhead or payload.

| Bit-7 | Bit-6 | Bit-5 | Bit-4 | Bit-3 | Bit-2 | Bit-1 | Bit-0 |
|---|---|---|---|---|---|---|---|
| Padding (0/2/4/6/8/10/12 bytes) | | | | | | | |
| Reserved | Reserved | Reserved | Reserved | CBI8 | CBI7 | CBI6 | CBI5 |
| CBI4 | CBI3 | CBI2 | CBI1 | Reserved | | | |
| Non ATM Payload/Padding | | | | | | | |

Figure 6. AsTriX Non-Standard ATM Cell Structure

Different from standard ATM cells, the source CBI port address is not carried in non-ATM cells.

PRIORITIZED CELL SWITCHING

A two level prioritized bus access scheme is used for cell switching between all the participating CBIs. Control traffic, high priority multicast and high priority unicast utilize high priority bus access to transfer cells and the rest utilize low priority for bus access. With this arrangement, even when the switch is overloaded, high priority traffic is guaranteed bus access.

Figure 7 below shows the priority mapping between ingress buffers, bus switch, and egress queues.

| Ingress Priority | Switch Priority | Egress Priority |
|---|---|---|
| Control | High | Control |
| Multicast High | | Multicast High |
| Unicast High | | Unicast High |
| Multicast Low | Low | Multicast Low |
| Unicast Low | | Unicast Low |

Figure 7. AsTriX Priority Mapping

SWITCH MEDIUM ACCESS CONTROL (MAC)

The switch employs a MAC protocol that allows all the switch ports access to the bus for cell switching. The MAC protocol is designed for two level prioritized asynchronous cell switching. Each CBI port utilizes two FIFO buffers to store cells coming from the UTOPIA Level 2 interface. The bus controller continuously issues fixed size free cells, or time slots onto the bus. When free cells flow downstream, they can be captured by active CBI ports for transferring cell payloads. This protocol provides a fair and efficient bus access between any number of ports through a free cell reservation mechanism.

Under circumstances of heavy traffic load in which multiple ports simultaneously access the bus, a Round-Robin cell access pattern between those active ports is generated. For such cases, the number of consecutive cell transmissions from any port is bounded by the total pipeline delay over all the CBI ports plus cell relay Proprietary iSwitch Corporation Information for use Sol y its Customers

AsTriX
TXC-05840            DATA SHEET            TRANSWITCH® delay experienced in the bus controller.

Each cell carries two address fields, source port address and destination port address. The destination port address specifies which CBI port needs to receive a cell payload. The destination address is only valid for unicast cell delivery. The source address denotes the cell originating port. Source address is not used in cell switching except for letting the bus controller know which source port a cell has originated from. In addition, the source address may be included in the UDF field of the cell when configured to do so by the configuration register during switch initialization.

Cells carrying statistics originated at each CBI port are always switched to host via the bus controller through high priority cell delivery. In other words, the bus controller intercepts all cells carrying CBI port statistics and feeds those directly to the host. A separate mail box is required for this bypassing mechanism.

UNICAST AND MULTICAST CELL DELIVERY

The switch supports both unicast and multicast cell deliveries. Unicast is performed via point-to-point cell delivery, a source CBI transfers a cell to a destination CBI. As far as cell delivery is concerned, unicast is implemented in two different ways, downstream cell delivery and upstream cell delivery. During downstream cell delivery, a source CBI transfers a cell to a destination CBI farther from the bus controller than the source along the bus direction. The cell is delivered to the destination CBI before it reaches the bus controller. An upstream cell delivery is a two step switching cycle. First, a source CBI transmits a cell to the bus controller. Upon receiving the cell, the bus controller then relays the cell back to the bus, so the destination CBI eventually receives the cell. The source CBI is responsible for filling the destination address field based on the destination address polled by an external UTOPIA Level 2 device.

The designation of multicast traffic receiving ports is determined by VPI values carried in individual multicast cells. For non-ATM cell, the multicast destination bitmap can be carried in a different location. Upon receiving a multicast cell, the ingress CBI copies the field carrying the multicast bitmap onto the MC_Bitmap field in the cell overhead area during AsTriX cell construction. Similar to upstream unicast cell delivery, multicast cell delivery is also a two-step process. First, a source CBI transmits a cell to the bus controller. Upon receiving the cell, the bus controller relays the cell to the bus. After one circulation of the cell along the bus, each CBI port receives the cell and uses the multicast bitmap carried in the MC_Bitmap field to determine whether or not it needs to receive the cell. Figure 8 shows the multicast bitmap arrangement for AsTriX *CellBus* expansion switch. Multicast function is solely designated to user traffic. In other words, CBI0, the host interface port, does not participate in multicast. If a bit is set in the bitmap carried in a cell, a corresponding CBI receives the multicast cell. Otherwise, the CBI simply bypasses the cell.

| CBI Port | 9-15 | 8 | 7 | 6 | 5 | 4 | 3 | 2 | 1 | 0 |
|---|---|---|---|---|---|---|---|---|---|---|
| | Reserved | 1/0 | 1/0 | 1/0 | 1/0 | 1/0 | 1/0 | 1/0 | 1/0 | 1/0 |

Figure 8. MC_Bitmap Field for Multicast Cell Delivery

Cell broadcast is a special case of cell multicast in which all the CBIs (CBI1-CBI8) receive, including source CBI, multicast cells. This feature is primarily useful for debugging. As far as implementation is concerned, cell broadcast is no different from cell multicast. Normally the source CBI does not receive broadcast cells. However, through bitmap setup, a source CBI can receive cells that originated from itself. The same holds true for multicast cell delivery.

Proprietary TranSwitch Corporation Information for use Solely by its Customers

TranSwitch® DATA SHEET

AsTriX
TXC-05840

CBI (*CELLBUS* INTERFACE) PORT

A CBI port is a full duplex switch port consisting of the following elements: 2 ingress FIFO queues, full duplex switch engine access, 5 egress FIFO queues, a flow control mechanism consisting of a counter array and a backpressure indicator, as well as a 16-bit mode UTOPIA Level 2 compliant interface. Figure 2 above provides an overall CBI block diagram from an architectural viewpoint.

For unicast traffic, the flow control mechanism is per egress queue based. For multicast traffic, however, it is global, or the entire switch based. A centralized 32-bit backpressure bitmap locates inside the switch engine to feed congestion status from egress queues to each CBI ingress port. For each priority level of multicast, a common UTOPIA port address is used for all CBI ports and a common backpressure bit is used.

Ingress Buffering

There are two ingress FIFO buffers to store and forward cells coming from the UTOPIA Level 2 interface. To prevent egress queue overflow, a counter array is employed to control the number of cells destined for each egress queue outstanding in each of the ingress queues. A counter is used to keep track of cells aiming at a particular egress queue. The cell counting for unicast traffic is per egress queue based and the counting for multicast traffic is global. For AsTriX with 8 ports, there are 16 counters for unicast traffic logging. In addition, there are 3 counters to record cells destined for the two multicast queues and the control traffic queue. As total, therefore, there are 19 such counters in the counter array.

All the high priority traffic including control, unicast and multicast traffic cells are forwarded to the high priority buffer for switching. Similarly, all the low priority traffic including both unicast and multicast are forwarded to the low priority buffer for switching. The queueing discipline is First-In-First-Out (FIFO). As long as high priority traffic is limited to a certain percentage of the overall traffic, high priority cells will always be switched without experiencing long buffer hold time.

When a cell arrives, regardless of which buffer it belongs to, a corresponding counter identified by the cell destination queue address increases by 1. When a cell leaves either queue, the same counter decreases by 1. Thus the counter records the number of cells outstanding in the buffer for a particular egress queue. A backpressure signal for each egress queue can be generated with respect to a predetermined counter threshold value. When a counter value reaches the threshold, a backpressure signal is asserted to stop the UTOPIA Level 2 interface from accepting any further cells destined for that particular egress queue. When the counter value decreases from the threshold, the backpressure signal is immediately de-asserted so that other cells towards that egress queue can be accepted.

Egress Queueing

As shown in Figure 2 above, each CBI egress includes 5 FIFO queues. Among these, 4 queues are dedicated to user traffic buffering and 1 queue is for control traffic. The queueing discipline follows fixed priority first in first out. The descending priority order is control traffic queue, high priority multicast queue, high priority unicast queue, low priority multicast queue and, finally, low priority unicast queue. The cell forward mechanism always exhausts cells in a higher priority queue before it forwards cells in lower priority queues.

All the queues dedicated to user traffic have identical depth. The queue dedicated to control traffic is smaller because the sole traffic source is the local host via a slave microprocessor interface access. But the size for each user traffic queue is deep enough to prevent queue overflow for the worst case scenario.

Backpressure signals are also generated by egress queues because of excessive cell accumulations. Actual backpressure signals are asserted when either ingress or egress congestion occurs. Between the two backpressure sources, a logical OR function is used for backpressure signal generation.

Proprietary iSwitch Corporation Information for use Solely by its Customers

AsTriX
TXC-05840          DATA SHEET                TranSwitch®

UTOPIA Level 2 Interface

Each CBI (CBI1-CBI8) uses standard UTOPIA Level 2 PHY emulation interface to connect devices such as CUBIT-3 (TXC-05804), CUBIT-622 (TXC-05805) and ASPEN (TXC-05810). Other off-the-shelf devices with standard UTOPIA Level 2 interface are also supported.

Address Conversion

The UTOPIA Level 2 receive interface is single-PHY. The UTOPIA Level 2 transmit interface supports 31 PHY addresses. In the AsTriX *CellBus* expansion switch, each individual egress queue uniquely maps to a UTOPIA Level 2 PHY address for unicast user traffic. For control traffic destined to the host, the UTOPIA address is 0. UTOPIA Level 2 addresses 1 and 2 are allocated for high and low priority multicast user traffic, respectively. Addresses 23 - 30 are reserved for configurations with more switch ports in the future. Figure 9 below lists the address mapping between UTOPIA interface and AsTriX ports.

| UTOPIA PHY Address | Egress Traffic Queue | CBI Port |
|---|---|---|
| 0 | Control | 0 |
| 1 | Multicast High Priority | 1 - 8 |
| 2 | Multicast Low Priority | 1 - 8 |
| 3 | Unicast High Priority | 1 |
| 4 | Unicast Low Priority | 1 |
| 5 | Unicast High Priority | 2 |
| 6 | Unicast Low Priority | 2 |
| 7 | Unicast High Priority | 3 |
| 8 | Unicast Low Priority | 3 |
| 9 | Unicast High Priority | 4 |
| 10 | Unicast Low Priority | 4 |
| 11 | Unicast High Priority | 5 |
| 12 | Unicast Low Priority | 5 |
| 13 | Unicast High Priority | 6 |
| 14 | Unicast Low Priority | 6 |
| 15 | Unicast High Priority | 7 |
| 16 | Unicast Low Priority | 7 |
| 17 | Unicast High Priority | 8 |
| 18 | Unicast Low Priority | 8 |
| 19 - 30 | Reserved | Reserved |

Figure 9. Address Mapping

Proprietary iSwitch Corporation Information for use Solely / its Customers

TranSwitch DATA SHEET

AsTriX
TXC-05840

Flow Control

Flow control is implemented at both ingress and egress directions. When either side encounters congestion, appropriate backpressure signals will be generated to stop cell inflow at one or multiple CBI ports.

Ingress Flow Control

The ingress flow control scheme, i.e., counter array based back-pressure mechanism, controls back-pressure generation and clearance locally. Any congestion occurring at one CBI port does not affect operations of any other CBI ports. The details of ingress back-pressure scheme is described in the Ingress Buffering section.

Egress Flow Control

Different from ingress flow control, egress backpressure is controlled globally. To perform cell switching between multiple ports and to support heterogeneous port speed switch configurations, each egress user traffic queue must be able to absorb burst traffic simultaneously coming from multiple ingress ports for a certain time period. To prevent cell overflow on any user traffic queue, a flow control scheme is used to feedback the queue congestion state from the egress direction to the ingress direction. When an egress queue accumulates cells up to a congestion threshold level, it raises a warning signal to generate backpressure as shown in Figure 10 below. Through the feedback mechanism, this will immediately trigger all ingress ports to stop accepting any further cells going to that congested egress queue.

To perform such flow control, each queue employs a congestion indicator. There are two parameters, minimum available space (MAS) and congestion clearance offset (CCO) associated with this congestion indicator. Parameter MAS is used for raising the congestion condition flag and parameter CCO is for clearing the congestion condition flag. Both parameters are user programmable. Parameter MAS is switch based and it is set globally. Parameter CCO is per port based and it is set individually. Users can change each parameter dynamically to optimize applications performance in terms of active port numbers and port rate. Figure 10 illustrates how the congestion indicator works in regard to these two parameters.

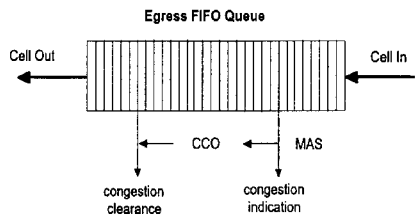

Figure 10. Egress Queue Based Flow Control

However, to prevent the head-of-line blocking, backpressure does not apply to ingress queues. In other words, cells already waiting in any ingress queues will be switched regardless of the backpressure bitmap changes.

After an egress queue gets congested, no more cells except those outstanding in ingress queues and in transi- Proprietary TranSwitch Corporation Information for use Solely by its Customers

**AsTriX
TXC-05840                    DATA SHEET                    TranSwitch®** tion on the bus will arrive at the queue. Stored cells will gradually leave the queue. When queue reduces to a congestion clearance point (queue size - MAS - CCO) the congestion indicator issues a congestion clearance signal. As a result, all the ingress ports resume accepting cells towards this once congested egress queue from external UTOPIA Level 2 devices. To prevent egress queue cell underflow, or starvation, this congestion clearance point must be a positive number. For UTOPIA Level 2 interface rate, the minimum congestion clearance point is 2. In AsTriX, from performance optimization standpoint, each port can have a separate CCO value.

For unicast traffic, each egress port maintains two independent flow control threads, one for high priority and one for low priority.

For multicast traffic, global (or switch) based flow control is chosen for the back pressure mechanism due to limited UTOPIA 2 address space (0 - 30). That is, a congestion occurring at one egress multicast queue enforces multicast backpressure to all ingress ports. Hence a congestion occurring at any egress queue for a particular priority forces all ingress ports to stop accepting any further multicast cells with this priority. For two priority levels, there are only two independent flow control threads.

Due to relatively slow control traffic being generated by host via slave access, flow control is not required. Because control traffic is given the highest priority on egress direction, a small egress queue will guarantee no cell overflow.

Egress Queue Timeout Mechanism for Multicast Traffic

During normal switch operation, external component malfunction or link failure associated with an egress port may cause stalling corresponding egress queues. For unicast traffic, cells accumulated in any unicast egress queue will eventually activate backpressure to ingress ports for stopping further traffic towards this particular queue. This will have no impact for traffic destined to unicast queues at other ports.

For multicast traffic, however, such occurrence will shut down all the multicast cell switching because of global backpressure handling mechanism. To avoid this scenario, an egress link status based timeout mechanism is available to prevent multicast backpressure from starving multicast traffic for an excessive time due to link failure experienced at a CBI egress port.

The timeout mechanism utilizes a timer to monitor the egress link status. A transmission of any cell from the egress port resets the timer. The timer is started when any egress queue is not empty and the transmission does not occur. A link failure is detected when the timer expires. In that case, the CBI port cancels both multicast backpressures regardless of congestion status. As a result, a link failure taking place at one CBI egress port will not affect multicast cell deliveries of the other CBI egress ports. The CBI egress port experiencing link failure will eventually drop all cells due to queue overflow.

Whenever a link failure is detected, the egress port generates an interrupt to the host (if not masked). The host is able to monitor relative statistics counters of user traffic to determine whether a link failure is recovered. The host can also issue control cells to test the condition of the egress port link status by checking the value change of the egress control counter.

The link status recovery is triggered by the transmission of either a unicast or a multicast cell. Upon such an instance, the CBI egress port resets the timeout timer and restores normal operation of the multicast backpressure mechanism.

The timeout value is determined during the switch initialization. The default value can be 1 or 2 ms, or any value around this range.

For any CBI ports not activated, cells coming from the switch bus are always dropped.

*Proprietary ⟩Switch Corporation Information for use Sol̴ y its Customers*

TranSwitch® DATA SHEET

AsTriX
TXC-05840

STATISTICS COLLECTION

There are two types of statistics to be collected: switch based (global) statistics and per CBI port based statistics. A counter is used for each statistics collection. To prevent any counter overflow, the host periodically reads all those statistics counters. When a counter reaches half full, i.e., the most significant bit changes from 0 to 1, it generates an interrupt to the host (if not masked). The host may mask such interrupts to avoid excessive interrupt processing.

Switch Based Statistics

The table below lists all switch based statistics that are collected:

| Name | Bits | Description |
| --- | --- | --- |
| TTC_GEN | 32 | Number of cells generated |
| TTC_USD | 32 | Number of cells used |
| TTC_UDLV | 32 | Number of unicast cells received |
| *TTC_RLY** | *32* | *Number of cells relayed* |
| TTC_MDLV | 32 | Number of multicast cells received |
| *TTC_HEXT** | *16* | *Number of control cells from CBI1-CBI8 to host* |
| *TTC_HINS** | *16* | *Number of control cells from host to CBI1-CBI8* |

*Note: Optional, specified for debugging purpose.

Proprietary iSwitch Corporation Information for use Solely by its Customers

AsTriX
TXC-05840           DATA SHEET           TRANSWITCH

CBI Port Based Statistics

The table below lists individual CBI port based statistics that are collected:

| Name | Bits | Description |
|---|---|---|
| EG_UC | 32 | Number of unicast cell outputs |
| EG_MC | 32 | Number of multicast cell outputs |
| EG_HOST | 16 | Number of control cell outputs |
| IG_UC | 32 | Number of unicast cell inputs |
| IG_MC | 32 | Number of multicast cell inputs |
| IG_HOST | 16 | Number of control cell inputs |
| CONG_UCHP | 32 | Number of high priority unicast egress queue congestions |
| CONG_UCLP | 32 | Number of low priority unicast egress queue congestions |
| CONG_MCHP | 32 | Number of high priority multicast egress queue congestions |
| CONG_MCLP | 32 | Number of low priority multicast egress queue congestions |

Proprietary ۱Switch Corporation Information for use Sol؎ ؍y its Customers

T̲R̲A̲N̲S̲W̲I̲T̲C̲H̲®　　　　　　　DATA SHEET　　　　　　　AsTriX
TXC-05840

OPERATION MODES

The AsTriX has four operation modes, the Reset Mode (RST_MODE), Initialization Mode (INIT_MODE), Normal Mode (NORMAL_MODE), and Diagnostic Mode (DIAG_MODE), as illustrated in Figure 3 above. Switch operation will be changed from one mode to the other upon issuance of command by the local host.

Reset Mode

Upon hardware reset (pin reset) the AsTriX is always in RST_MODE. In this mode, all the registers, statistics counters, and state machines are in their reset state. Each CBI has no knowledge about its port number, nor does the bus controller know the total number of CBI ports in the switch chip. The only meaningful command is INIT_SW, which forces the AsTriX into INIT_MODE.

The local host may choose to reset the AsTriX by issuing a RST_SW command when AsTriX is in the INIT_MODE, or NORMAL_MODE or DIAG_MODE known as software reset.

Initialization Mode

When AsTriX enters this mode from RST_MODE, a port number assignment procedure will be performed automatically, which is described as follows.

BC will issue a cell to carry the INIT_SW command for all the CBI ports, with the Total Port Number field of zero (TPN = 0). When this cell travels along the looped bus, each CBI port in the RST_MODE will take the following action. The CBI0 will just bypass the cell, and the other CBI port (CBI1 ~ CBI8) will increase TPN value (of the incoming cell) by one, then relay the cell to the next CBI port. The CBI port will also take the new value as its port number. This cell will eventually reach the BC with the total number of ports in the TPN field, upon which the AUTO_INIT_DONE bit in the Switch Status Register will be set, and the TPN field will be copied into the corresponding bits in the register. the AUTO-Port-ASSignment interrupt (AUTO_PASS) will be generated if not masked upon completion of this procedure.

A timer in BC and an error bit in the INT_BC register are included to deal with abnormal conditions for this procedure. When BC sends the cell in the RST_MODE, it also starts the timer. If BC cannot receive the cell upon timer expiration, the error bit will be set. An interrupt will be generated if not masked upon time out. The switch chip will not be useful if this error occurs.

In the INIT_MODE, all the CBI ports are still disabled, and all the statistics counters maintain their reset value. The only meaningful commands are RST_SW, EN_SW and DIAG_SW. In the INIT_MODE, the AsTriX will be forced into RST_MODE upon receiving RST_SW command, or into NORMAL_MODE upon EN_SW command, or into DIAG_MODE upon DIAG_SW command.

Entrance of INIT_MODE also can happen from NORMAL_MODE or DIAG_MODE upon issuance of INIT_SW command. But either event will not trigger an auto port number assignment procedure as from RST_MODE.

Normal Mode

The NORMAL_MODE can only be entered from INIT_MODE, and all the CBI ports are inactive after the mode change. Each CBI port can be activated, or deactivated (after activation). When CBI port is inactive, it only bypasses the cell.

Normally, the local host will program the low watermark register and per port watermark offset register before enabling the CBI port. But Dynamic Port Activation is also supported, after reception of SET_WM_OFFSET or SET_LOW_WM command.

All the commands (except DIAG_SW) are applicable in NORMAL_MODE. All the statistics counter value, table contents, and switch/port status can be polled by reading the registers, or through mailbox scheme.

The AsTriX in the NORMAL_MODE can be forcefully reset (enter RST_MODE) upon receiving a RST_SW Proprietary iSwitch Corporation Information for use Sol / its Customers

AsTriX
TXC-05840      DATA SHEET      TRANSWITCH® command, or gracefully reset upon INIT_SW command. It is recommended that host should disable all the ports before entering INIT_MODE. All the LOW_WM and WM_OFFSET settings are maintained for NORM_MODE to INIT_MODE transition.

Diagnostic Mode

This mode provides semi-automatic at-speed internal data-path check (BIST), and enables UTOPIA interface loop back testing during debugging or system diagnostic procedure.

The local host will issue/re-issue BIST command with different parameters to address different data paths. Detailed description should be found in the command description. Upon reception of a BIST command, the BC will generate a sequence of test cells, passing through different data paths (IG and EG queues), and eventually receive those cells and check for the correctness. The AUTO_PASS interrupt bit will be used in the DIAG_MODE to flag the successful completion of each test.

If the test cells are not completely received or the cell content is incorrect, a corresponding interrupt bit will be set in the INT_BC register, and INTR# will be asserted if not masked.

If errors occur, the AsTriX should be forced into RST_MODE with RST_SW command, and the chip will not be useful. If no errors occur, the AsTriX can be programmed to enter NORMAL_MODE through INIT_MODE.

All the statistics counter values will keep their reset values in this mode. The only meaningful commands in this mode are BIST, RST_SW, or INIT_SW.

Proprietary TranSwitch Corporation Information for use Solely by its Customers

TRANSWITCH®      DATA SHEET      AsTriX TXC-05840

MICROPROCESSOR INTERFACE AND MAILBOXES

The AsTriX *CellBus* expansion switch integrates a 16-bit microprocessor, or host interface for transferring data and control information. This interface is Motorola MPC850/860 and 68xxx microprocessor compatible with big endian bit. This interface permits a host processor to configure the AsTriX *CellBus* expansion switch and obtain statistics from bus controller and each CBI port. Management traffic is also inserted and extracted by the host through this interface to communicate with remote processors connected to CUBIT-3 (TXC-05804), CUBIT-622 (TXC-05805), ASPEN (TXC-05810) or other devices.

There are three 64-byte mailboxes implemented to realize host-insertion, host-extraction, and status/counter value retrieving. Each mail box is associated with a status register. Two commands are also used to support the mailbox scheme, the PUT_MB command is used in mailbox stuffing while the GET_MB command in mailbox retrieving.

The host insertion is supported by the transmit mailbox (TX_MB) and a TX Mailbox status register. To do the insertion, the host will first issue a PUT_MB (with start option) command to lock the transmit mailbox, then write the contents into the mailbox (1 - 32 word). The host must release the mailbox by issuing another PUT_MB (with end option) command. The status of TX_MB can be monitored by reading the TX Mailbox status register. This scheme supports multi-task/multi-thread programs. Details can be found in the description of PUT_MB command and TX Mailbox status register in the 'Register Definition and Host Access' section.

.The host extraction is supported by a 64-byte receive mailbox (RX_MB_H) and a RX Mailbox (from remote host) status register. When the receive mailbox receives a cell from a remote host through an internal buffer, an interrupt will be generated if not masked. Also, the valid bit in the mailbox register will be set. The host will read the contents (1 -32 word) from the mailbox once alerted by interrupt or polling mechanism. The host will then return the mailbox by issuing a GET_MB_H command. The status of RX_MB_H mailbox can be monitored by reading the RX Mailbox status register. This scheme supports multi-task/multi-thread programs. Details can be found in the description of GET_MB command and RX Mailbox status register in the 'Register Definition and Host Access' section.

The other receive mailbox (RX_MB_L) will be used for polling of chip status, statistics counters, and the TX_MB contents (for debugging). One cell of information held in the RX_MB_L is also referred as a page (64-byte) in the following discussion. There is one page for global (per chip) statistics counters and 1 page of status and statistics counter information for each port. Details of operation can be found in the description of GET_MB command and RX Mailbox status register in the 'Register Definition and Host Access' section.

Proprietary Switch Corporation Information for use Sol / its Customers

AsTriX
TXC-05840               DATA SHEET                TRANSWITCH®

BOUNDARY SCAN

A Boundary Scan Description Language (BSDL) file for the AsTriX device is available for download from the Products page of the TranSwitch Internet Web site at www.transwitch.com.

Introduction

The IEEE 1149.1 standard defines the requirements of a boundary scan architecture that has been specified by the IEEE Joint Test Action Group (JTAG). Boundary scan is a specialized scan architecture that provides observability and controllability for the interface leads of the device. As shown in Figure 11, one cell of a boundary scan register is assigned to each input or output lead to be observed or tested (bidirectional leads may have two cells). The boundary scan capability is based on a Test Access Port (TAP) controller, instruction and bypass registers, and a boundary scan register bordering the input and output leads. The boundary scan test bus interface consists of four input signals (Test Clock (TCK), Test Mode Select (TMS), Test Data Input (TDI) and Test Reset ($\overline{TRS}$)) and a Test Data Output (TDO) output signal. Boundary scan signal timing is shown in Figure 17.

The TAP controller receives external control information via a Test Clock (TCK) signal and a Test Mode Select (TMS) signal, and sends control signals to the internal scan paths. The TAP controller is reset by asserting the $\overline{TRS}$ lead low for a minimum of 5 nanoseconds. Detailed information on the operation of this state machine can be found in the IEEE 1149.1 standard. The serial scan path architecture consists of an instruction register, a boundary scan register and a bypass register. These three serial registers are connected in parallel between the Test Data Input (TDI) and Test Data Output (TDO) signals, as shown in Figure 11.

The boundary scan function will be reset and disabled by holding lead $\overline{TRS}$ low. When boundary scan testing is not being performed the boundary scan register is transparent, allowing the input and output signals to pass to and from the AsTriX device's internal logic. During boundary scan testing, the boundary scan register may disable the normal flow of input and output signals to allow the device to be controlled and observed via scan operations.

Boundary Scan Operation

The maximum frequency the AsTriX device will support for boundary scan is 10 MHz. The timing diagrams for the boundary scan interface leads are shown in Figure 17.

The instruction register contains three bits. The AsTriX device performs the following three boundary scan test instructions:

The EXTEST test instruction (000) provides the ability to test the connectivity of the AsTriX device to external circuitry.

The SAMPLE test instruction (010) provides the ability to examine the boundary scan register contents without interfering with device operation.

The BYPASS test instruction (111) provides the ability to bypass the AsTriX boundary scan and instruction registers.

During the *Capture - IR* state, a fixed value (101) is loaded into the instruction register.

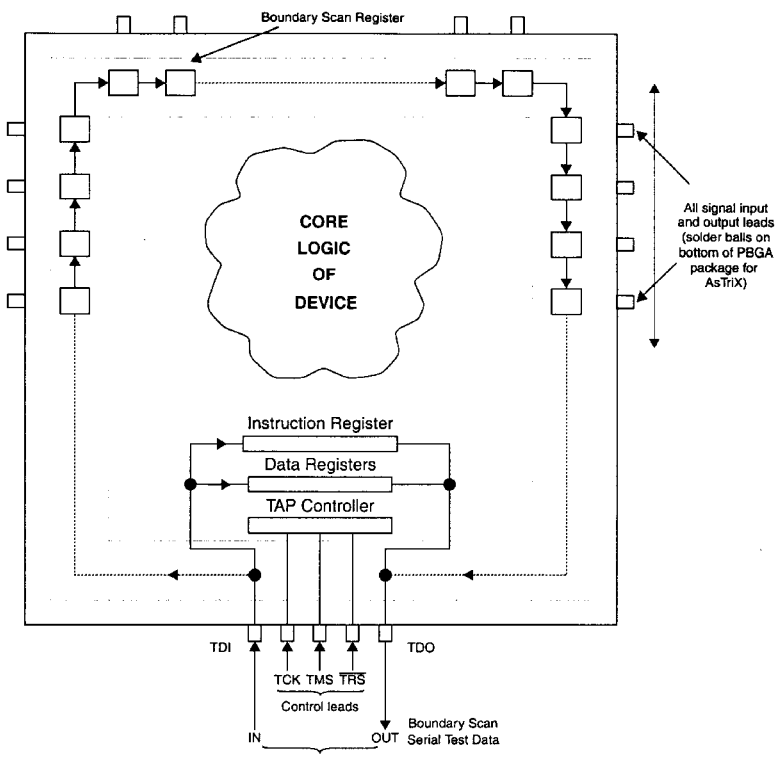
Figure 11. Boundary Scan Top-Level Block Diagram

Proprietary TranSwitch Corporation Information for use Solely by its Customers

AsTriX
TXC-05840  DATA SHEET  TranSwitch®

LEAD DESCRIPTIONS

POWER SUPPLY, GROUND AND NO CONNECT LEADS

| Symbol | Lead No. | I/O/P* | Type | Name/Function |
|---|---|---|---|---|
| VDD3.3 | E6, E25, F5, F7, F8, F11, F14, F15, F16, F17, F20, F23, F24, F26, G6, G25, H6, H25, L6, L25, P6, P25, R6, R25, T6, T25, U6, U25, Y6, Y25, AC6, AC25, AD6, AD25, AE5, AE7, AE8, AE11, AE14, AE15, AE16, AE17, AE20, AE23, AE24, AE26, AF6, AF25 | P | | $V_{DD}$: +3.3 volt I/O power supply, ±5% |
| VDD1.8 | E7, E8, E23, E24, F9, F10, F12, F13, F18, F19, F21, F22, G5, G26, H5, H26, J6, J25, K6, K25, M6, M25, N6, N25, V6, V25, W6, W25, AA6, AA25, AB6, AB25, AC5, AC26, AD5, AD26, AE9, AE10, AE12, AE13, AE18, AE19, AE21, AE22 AF7, AF8, AF23, AF24 | P | | $V_{DD}$: +1.8 volt core power supply, ±5% |
| VSS | A1, A30, B2, B29, C3, C28, D4, D27, E5, E26, F6, F25, M12, M13, M14, M15, M16, M17, M18, M19, N12, N13, N14, N15, N16, N17, N18, N19, P12, P13, P14, P15, P16, P17, P18, P19, R12, R13, R14, R15, R16, R17, R18, R19, T12, T13, T14, T15, T16, T17, T18, T19, U12, U13, U14, U15, U16, U17, U18, U19, V12, V13, V14, V15, V16, V17, V18, V19, W12, W13, W14, W15, W16, W17, W18, W19, AE6, AE25, AF5, AF26, AG4, AG27, AH3, AH28, AJ2, AJ29, AK1, AK30 | P | | $V_{SS}$: Ground, 0 volt reference. |
| PLLAVDD | A2 | P | | PLL Core Analog +1.8 volt power supply, ±5%. |
| PLLAVSS | C4 | P | | PLL Core Analog 0.0 volt reference. |
| PLLDVDD | D5 | P | | PLL Core Digital +1.8 volt power supply, ±5% |
| PLLDVSS | A3 | P | | PLL Core Digital 0.0 volt reference. |
| PLLVDD | E9 | P | | PLL +3.3 volt I/O power supply, ±5%. |
| PLLVSS | B4 | P | | PLL 0.0 volt I/O reference. |
| NC | E20, E21, E22, J5, J26, K5, K26, L5, L26, M5, U26, Y5, AA26, AB26, AF15, AF20, AF21, AF22 | -- | | No Connect: NC leads are not to be connected, not even to another NC lead, but must be left floating. Connection of NC leads may impair performance or cause damage to the device. Some NC leads may be assigned functions in future upgrades of the device. |

* Note: I=Input; O=Output; P=Power; T=Tristate

*Proprietary TranSwitch Corporation Information for use Solely by its Customers*

TranSwitch® DATA SHEET

**AsTriX
TXC-05840**

SYSTEM

| Symbol** | Lead No. | I/O/P | Type* | Name/Function |
|---|---|---|---|---|
| SCLK | C5 | I | TTL | System Clock Input: 50 MHz input clock. |
| SRESET | B3 | I | TTL | System Reset: Active low device reset (minimum duration 300 nanoseconds). |

\* See Input, Output and Input/Output Parameters section for Type definitions.
\*\* Signals which are active when low or upon their falling edges are shown as negated (overlined).

SWITCH PORT n INTERFACE (n = 1 to 8)

| Symbol | Lead No. | I/O/P | Type | Name/Function |
|---|---|---|---|---|
| RXnCLKI | A29, R26, AJ30, AH17, AK2, P1, C2, B16 | I | LVTTL | Port n Egress Terminal UTOPIA Clock: 50 MHz UTOPIA Interface input clock. |
| RXnENB | B28, R27, AH29, AK18, AJ3, R4, D3, A16 | I | LVTTL | Port n Egress Terminal Enable: Active low read enable signal for cell input. |
| RXnSOC | C27, P30, AG28, AG17, AH4, R5, B1, A15 | O | TTL 8 mA | Port n Egress Terminal Start of Cell: Start of Cell Indicator. |
| RX1DATA(0-15) | D26, A28, B27, D25, C26, A27, B26, D24, C25, A26, B25, C24, D23, A25, B24, C23 | O | TTL 8 mA | Port n Egress Terminal Data: Output data bus. |
| RX2DATA(0-15) | P29, P28, N30, P27, N29, P26, N28, M30, M29, N27, M28, L30, L29, N26, L28, M27 | | | |
| RX3DATA(0-15) | AF27, AH30, AG29, AE27, AF28, AG30, AF29, AD27, AE28, AF30, AE29, AD28, AC27, AE30, AD29, AC28 | | | |
| RX4DATA(0-15) | AJ18, AH18, AF17, AK19, AJ19, AG18, AH19, AK20, AJ20, AG19, AH20, AK21, AF18, AK22, AJ21, AG20 | | | |

Proprietary iSwitch Corporation Information for use Sol / its Customers

AsTriX
TXC-05840　　　　　　　　DATA SHEET　　　　　　　TRANSWITCH

| Symbol | Lead No. | I/O/P | Type | Name/Function |
|---|---|---|---|---|
| RX5DATA(0-15) | AG5, AK3, AJ4, AG6, AF9, AH5, AK4, AJ5, AG7, AH6, AK5, AJ6, AH7, AF10, AG8, AK6 | O | TTL 8 mA | Port n Egress Terminal Data: Output data bus. |
| RX6DATA(0-15) | R3, R2, R1, T1, T2, T3, T4, T5, U1, U2, U3, V1, U4, V2, V3, U5 | | | |
| RX7DATA(0-15) | E4, C1, D2, E3, F4, D1, E2, G4, F3, E1, F2, G3, H4, G2, F1, H3 | | | |
| RX8DATA(0-15) | B15, C15, E15, D15, A14, B14, C14, A13, D14, B13, E14, C13, A12, B12, D13, C12 | | | |
| RXnPRTY | D22, K29, AB27, AH21, AJ7, W1, J4, A11 | O | TTL 8 mA | Port n Egress Terminal Parity: Odd parity over RXnDATA(0-15). |
| RXnCLAV | A24, K30, Y26, AJ22, AH8, W2, G1, B11, | O | TTL 8 mA | Port n Egress Terminal Cell Available: Active high signal indicating that a cell is available. |
| TXnCLKI | B23, J30, AD30, AF19, AG9, V4, H2, E13, | I | LVTTL | Port n Ingress Terminal UTOPIA Clock: 50 MHz UTOPIA Interface input clock. |
| TXnENB | C22, L27, AC29, AK23, AK7, W3, J3, D12 | I | LVTTL | Port n Ingress Terminal Enable: Active low read enable signal for cell input. |
| TXnSOC | D21, K28, AB28, AG21, AF11, Y1, K4, C11 | I | LVTTL | Port n Ingress Terminal Start of Cell: Start of Cell Indicator. |

| Symbol | Lead No. | I/O/P | Type | Name/Function |
|---|---|---|---|---|
| TX1DATA(0-15) | E19, A23, C21, B22, D20, A22, B21, C20, A21, E18, D19, B20, A20, C19, D18, E17 | I | LVTTL | Port n Ingress Terminal Data: Input data bus. |
| TX2DATA(0-15) | M26, J29, H30, K27, J28, H29, G30, J27, H28, G29, F30, H27, G28, F29, E30, F28 | | | |
| TX3DATA(0-15) | AA27, AC30, AB29, W26, AA28, Y27, AB30, AA29, AA30, Y28, W27, V26, Y29, Y30, W28, V27 | | | |
| TX4DATA(0-15) | AH22, AJ23, AK24, AG22, AH23, AJ24, AK25, AG23, AH24, AJ25, AK26, AH25, AG24, AJ26, AK27, AH26 | | | |
| TX5DATA(0-15) | AJ8, AH9, AG10, AK8, AJ9, AH10, AF12, AG11, AK9, AJ10, AK10, AH11, AG12, AJ11, AF13, AK11 | | | |
| TX6DATA(0-15) | Y2, W4, V5, Y3, AA1, AA2, Y4, AB1, AA3, AB2, W5, AC1, AA4, AB3, AC2, AD1 | | | |
| TX7DATA(0-15) | J2, H1, K3, L4, J1, K2, K1, L3, N5, M4, L2, L1, M3, N4, M2, M1 | | | |
| TX8DATA(0-15) | A10, B10, A9, D11, E12, C10, B9, A8, D10, C9, B8, A7, E11, D9, C8, B7 | | | |
| TXnPRTY | B19, G27, W29, AG25, AH12, AB4, N3, A6 | I | LVTTL | Port n Ingress Terminal Parity: Odd parity over TXnDATA(0-15). |

Proprietary Switch Corporation Information for use Sol‹ ‹ its Customers

AsTriX
TXC-05840  DATA SHEET  TRANSWITCH®

| Symbol | Lead No. | I/O/P | Type | Name/Function |
|---|---|---|---|---|
| TX1ADDR(0-4) | A19, C18, B18, D17, A18 | I | LVTTL | Port n Ingress Address: Used for polling each port to determine the availability of cell space, and for selection of ports for transmit side. |
| TX2ADDR(0-4) | E29, D30, E28, F27, D29 | | | |
| TX3ADDR(0-4) | W30, V28, V29, U27, V30 | | | |
| TX4ADDR(0-4) | AJ27, AK28, AG26, AH27, AJ28 | | | |
| TX5ADDR(0-4) | AG13, AJ12, AK12, AH13, AJ13 | | | |
| TX6ADDR(0-4) | AC3, AD2, AE1, AC4, AD3 | | | |
| TX7ADDR(0-4) | P5, N2, P4, N1, P3 | | | |
| TX8ADDR(0-4) | D8, C7, B6, E10, A5 | | | |
| TXnCLAV | C17, C30, U28, AK29, AF14, AA5, P2, C6 | O | TTL 8 mA | Port n Ingress Terminal Cell Available: Active high signal indicating that a cell is available. |

LED INTERFACE

| Symbol | Lead No. | I/O/P | Type | Name/Function |
|---|---|---|---|---|
| CHIPLED(0-1) | T26, T27 | O(T) | TTL 16 mA | Two LED leads for device status, active low. Low Low - Normal Mode; Low High - Initialization Mode; High Low - Diagnostic Mode; High High - Reset Mode |
| PORTLED(0-7) | T30, R30, R29, R28, E27, D28, C29, B30 | O(T) | TTL 16 mA | Eight LED leads for port status, active low; Low - Port enabled; High - Port disabled |

MICROPROCESSOR INTERFACE

| Symbol | Lead No. | I/O/P | Type | Name/Function |
|---|---|---|---|---|
| PCLK | AF4 | I | TTL | Processor Clock: Rising edge used for data transfer. The maximum frequency of this clock is 50 MHz. |
| A(0-8) | AE3, AD4, AF2, AG1, AF3, AE4, AB5, AG2, AH1 | I | TTL | Address Bus: 9-bit address lines from microprocessor, used to address AsTriX register memory. A0 is LSB. High is logic 1. |

*Proprietary TranSwitch Corporation Information for use Solely by its Customers*

TranSwitch®     DATA SHEET     AsTriX TXC-05840

| Symbol | Lead No. | I/O/P | Type | Name/Function |
|---|---|---|---|---|
| R/W | AG3 | I | TTL | Read/Write: Data transfer command for AsTriX memory. Read (high) / Write (low) for Motorola. |
| D(0-15) | AG14, AK13, AH14, AJ14, AK14, AG15, AH15, AJ15, AK15, AK16, AJ16, AH16, AG16, AF16, AK17, AJ17 | I/O(T) | TTL/ TTL 8 mA | Data Bus: Bidirectional 16-bit data lines used for transferring data to and from microprocessor. D0 is LSB. High is logic 1. |
| TS | AH2 | I | TTL | Transfer Start: (Active low) Asserted by MC860/850 to indicate the start of a bus cycle. |
| TA | AJ1 | O(T) | TTL 16 mA | Transfer Acknowledge: Active low Data Transfer Acknowledge. Asserted by slave device to indicate termination of the bus cycle. |
| INTREQ | AF1 | O | TTL 8 mA | Interrupt Request: (Active low) Interrupt request to the MC860/850 (level sensitive). |
| CS | AE2 | I | TTL | Chip Select: Active low signal for chip selection. |

RESET AND TEST LEADS (INCLUDING TEST ACCESS PORT FOR BOUNDARY SCAN)

| Symbol | Lead No. | I/O/P | Type | Name/Function |
|---|---|---|---|---|
| TDO | C16 | O(T) | TTL 16 mA | JTAG Data Output: Output for data and test instructions from internal test registers for Boundary Scan. |
| TRS | B17 | I | LVTTLp | JTAG Mode Reset: A 1 microsecond (minimum) low on this lead resets the boundary scan; recommended for power-up initialization as well. |
| TMS | E16 | I | LVTTLp | JTAG Mode Select: Mode select for Boundary Scan. |
| TDI | D16 | I | LVTTLp | JTAG Data Input: Data and test instruction input for Boundary Scan. |
| TCK | A17 | I | LVTTL | JTAG Clock: Clocks in TMS and TDI signals on rising edge. |
| PLLBYPASS | A4 | I | TTL | Test Select for digital test (by passing PLL): Bypass the PLL for manufacturing test. Low - Normal Mode High - Test Mode |
| PLLCLOCK | D6 | O | TTL 8 mA | PLL clock output: A divided by 4 clock from PLL (for PLL test) |

Proprietary Switch Corporation Information for use Sol/its Customers

AsTriX
TXC-05840                        DATA SHEET                        TRANSWITCH®

| Symbol | Lead No. | I/O/P | Type | Name/Function |
|---|---|---|---|---|
| PLLFB(0-1) | D7, B5 | I | TTL | PLL frequency multiplication selection:<br>Low Low - 125 MHz<br>Low High - 175 MHz<br>High Low - 150 MHz<br>High High - 200 MHz |
| SCANEN | U30 | I | TTL | Scan Enable: Internal test function. Tie to $V_{SS}$. |
| TESTEN | U29 | I | TTL | Scan Test Enable: This lead is used for factory test. Tie to $V_{SS}$. |
| BISTCLKI | T28 | I | TTL | BIST Clock: Internal memory BIST Clock. |
| BISTEN | T29 | I | TTL | BIST Enable: Internal memory BIST Enable. |

*Proprietary TranSwitch Corporation Information for use Solely by its Customers*

TRANSWITCH®     DATA SHEET     AsTriX TXC-05840

ABSOLUTE MAXIMUM RATINGS AND ENVIRONMENTAL LIMITATIONS

| Parameter | Symbol | Min | Max | Unit | Conditions |
|---|---|---|---|---|---|
| Core Supply Voltage, +1.8V nominal | $V_{DD1.8}$ | -0.3 | 2.1 | V | Notes 1, 4 |
| I/O Supply Voltage, +3.3V nominal | $V_{DD3.3}$ | -0.3 | 3.9 | V | Notes 1, 4 |
| DC input voltage | $V_{IN}$ | -0.5 | 6.0 | V | Notes 1, 4 |
| Output Voltage | $V_{out}$ | -0.5 | 4.6 | V | Notes 1, 4 |
| Storage temperature range | $T_S$ | -55 | 150 | °C | Note 1 |
| Ambient operating temperature | $T_A$ | -40 | 85 | °C | 0 ft/min. linear airflow |
| Moisture Exposure Level | ME | 5 | | Level | per EIA/JEDEC JESD22-A112-A |
| Relative humidity, during assembly | RH | 30 | 60 | % | Note 2 |
| Relative humidity, in-circuit | RH | 0 | 100 | % | non-condensing |
| ESD Classification | ESD | absolute value 2000 | | V | Note 3 |
| Latch-Up | LU | | | | Meets JEDEC STD-78 |

Notes:
1. Conditions exceeding the Min or Max values may cause permanent failure. Exposure to conditions near the Min or Max values for extended periods may impair device reliability.
2. Pre-assembly storage in non-drypack conditions is not recommended. Please refer to the instructions on the "CAUTION" label on the drypack bag in which devices are supplied.
3. Test method for ESD per MIL-STD-883D, Method 3015.7.
4. Device core is 1.8V only.

THERMAL CHARACTERISTICS

| Parameter | Min | Typ | Max | Unit | Test Conditions |
|---|---|---|---|---|---|
| Thermal resistance - junction to ambient | | 14.5 | | °C/W | 0 ft/min linear airflow |

POWER REQUIREMENTS

| Parameter | Min | Typ | Max | Unit | Test Conditions |
|---|---|---|---|---|---|
| $V_{DD3.3}$ | 3.15 | 3.3 | 3.45 | V | |
| $I_{DD3.3}$ | | | TBD | mA | See Notes 1 and 2 |
| $P_{DD3.3}$ | | | TBD | W | See Notes 1 and 2 |
| $V_{DD1.8}$ | 1.71 | 1.8 | 1.89 | V | |
| $I_{DD1.8}$ | | | TBD | mA | See Notes 1 and 2 |
| $P_{DD1.8}$ | | | TBD | W | See Notes 1 and 2 |

Notes:
1. Typical values are based on measurements made with nominal voltages at 25° C
2. All $I_{DD}$ and $P_{DD}$ values are dependent upon $V_{DD}$.

*PRODUCT PREVIEW*

Proprietary Switch Corporation Information for use Sol / its Customers

AsTriX
TXC-05840          DATA SHEET          TRANSWITCH®

INPUT, OUTPUT AND INPUT/OUTPUT PARAMETERS

INPUT PARAMETERS FOR LVTTL

| Parameter | Min | Typ | Max | Unit | Test Conditions |
|---|---|---|---|---|---|
| $V_{IH}$ | 2.0 | | | V | $3.15 \leq V_{DD} \leq 3.45$ |
| $V_{IL}$ | | | 0.8 | V | $3.15 \leq V_{DD} \leq 3.45$ |
| Input leakage current | | | 10 | µA | $V_{DD}=3.45$, $V_{IN}=0$ to 3.45 |
| Input capacitance | | 5 | | pF | |

INPUT PARAMETERS FOR LVTTLp (TTL WITH INTERNAL PULL-UP)

| Parameter | Min | Typ | Max | Unit | Test Conditions |
|---|---|---|---|---|---|
| $V_{IH}$ | 2.0 | | | V | $3.15 \leq V_{DD} \leq 3.45$ |
| $V_{IL}$ | | | 0.8 | V | $3.15 \leq V_{DD} \leq 3.45$ |
| Input current | -35 | -115 | -214 | µA | $V_{IN}=V_{SS}$ |
| Input leakage current | | | 10 | µA | $V_{IN}=V_{DD}$ |
| Input capacitance | | 5 | | pF | |

INPUT PARAMETERS FOR TTL

| Parameter | Min | Typ | Max | Unit | Test Conditions |
|---|---|---|---|---|---|
| $V_{IH}$ | 2.0 | | | V | $3.15 \leq V_{DD} \leq 3.45$ |
| $V_{IL}$ | | | 0.8 | V | $3.15 \leq V_{DD} \leq 3.45$ |
| Input leakage current | | | 7.0 | nA | $V_{DD}=3.45$, $V_{IN}=0$ to 3.45 |
| Input capacitance | | 5 | | pF | |

*Proprietary TranSwitch Corporation Information for use Solely by its Customers*

TranSwitch  DATA SHEET  AsTriX TXC-05840

OUTPUT PARAMETERS FOR TTL 8 mA

| Parameter | Min | Typ | Max | Unit | Test Conditions |
|---|---|---|---|---|---|
| $V_{OH}$ | 2.4 | | | V | $V_{DD} = 3.15$; $I_{OH} = -4.0$ |
| $V_{OL}$ | | 0.2 | 0.4 | V | $V_{DD} = 3.15$; $I_{OL} = 4.0$ |
| Tristate leakage current | -10 | | 10 | µA | |
| $I_{OL}$ | | | 8.0 | mA | |
| $I_{OH}$ | | | -8.0 | mA | |

INPUT/OUTPUT PARAMETERS FOR TTL/TTL 8 mA

| Parameter | Min | Typ | Max | Unit | Test Conditions |
|---|---|---|---|---|---|
| $V_{IH}$ | 2.0 | | | V | $3.15 \leq V_{DD} \leq 3.45$ |
| $V_{IL}$ | | | 0.8 | V | $3.15 \leq V_{DD} \leq 3.45$ |
| Input leakage current | | | 8.0 | nA | $V_{DD} = 3.45$ |
| Input capacitance | | 7 | | pF | |
| $V_{OH}$ | 2.4 | | | V | $V_{DD} = 3.15$; $I_{OH} = -8.0$ |
| $V_{OL}$ | | | 0.4 | V | $V_{DD} = 3.15$; $I_{OL} = 8.0$ |
| $I_{OL}$ | | | 8.0 | mA | |
| $I_{OH}$ | | | -8.0 | mA | |

INPUT/OUTPUT PARAMETERS FOR TTL/TTL 16 mA

| Parameter | Min | Typ | Max | Unit | Test Conditions |
|---|---|---|---|---|---|
| $V_{IH}$ | 2.0 | | | V | $3.15 \leq V_{DD} \leq 3.45$ |
| $V_{IL}$ | | | 0.8 | V | $3.15 \leq V_{DD} \leq 3.45$ |
| Input leakage current | | | 8.0 | nA | $V_{DD} = 3.45$ |
| Input capacitance | | 7 | | pF | |
| $V_{OH}$ | 2.4 | | | V | $V_{DD} = 3.15$; $I_{OH} = -16.0$ |
| $V_{OL}$ | | | 0.4 | V | $V_{DD} = 3.15$; $I_{OL} = 16.0$ |
| $I_{OL}$ | | | 16.0 | mA | |
| $I_{OH}$ | | | -16.0 | mA | |

*PRODUCT PREVIEW*

Proprietary Switch Corporation Information for use Sol / its Customers

AsTriX
TXC-05840 DATA SHEET TranSwitch

TIMING CHARACTERISTICS

Detailed timing diagrams for the AsTriX device are provided in Figures 12 through 17, with values for the timing intervals given in tables below the waveform drawings. All output times are measured with a maximum 25 pF load capacitance, unless noted otherwise. Timing parameters are measured at voltage levels of $(V_{IH}+V_{IL})/2$ and $(V_{OH}+V_{OL})/2$, for input and output signals, respectively.

Figure 12. Timing of UTOPIA Transmit Multi-PHY (PHY Layer Emulation) (16-bit)

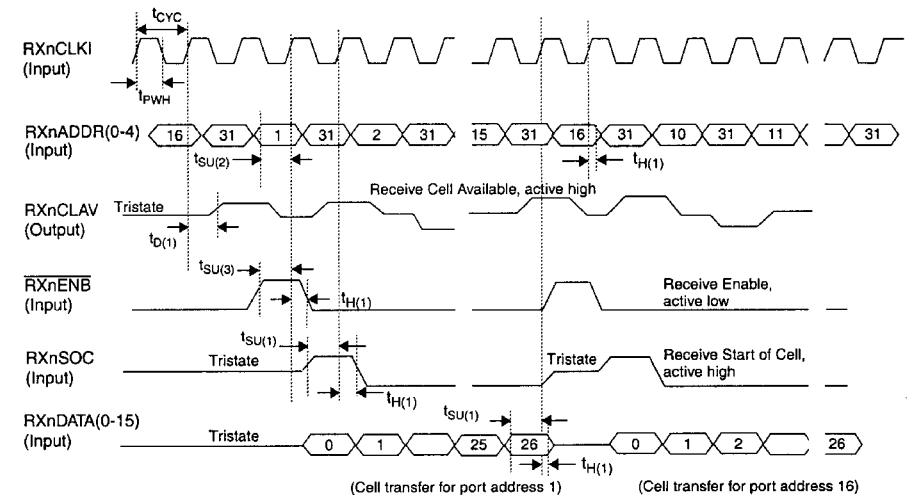

| Parameter | Symbol | Min | Typ | Max | Unit |
|---|---|---|---|---|---|
| RXnCLKI clock cycle time | $t_{CYC}$ | 20 | | | ns |
| RXnCLKI duty cycle, $t_{PWH}/t_{CYC}$ | | 40 | | 60 | % |
| RXnDATA(0-15), RXnSOC setup time to RXnCLKI↑ | $t_{SU(1)}$ | 4.0 | | | ns |
| RXnADDR(0-4) setup time to RXnCLKI↑ | $t_{SU(2)}$ | 5.0 | | | ns |
| RXnENB setup time to RXnCLKI↑ | $t_{SU(3)}$ | 6.0 | | | ns |
| RXnDATA(0-15), RXnSOC, RXnADDR(0-4), RXnENB hold time after RXnCLKI↑ | $t_{H(1)}$ | 1.0 | | | ns |
| RXnCLAV delay from RXnCLKI↑ | $t_{D(1)}$ | 2.0 | | 12 | ns |

*Proprietary TranSwitch Corporation Information for use Solely by its Customers*

TranSwitch®     DATA SHEET     AsTriX TXC-05840

Figure 13. Timing of UTOPIA Receive Multi-PHY (PHY Layer Emulation) (16-bit)

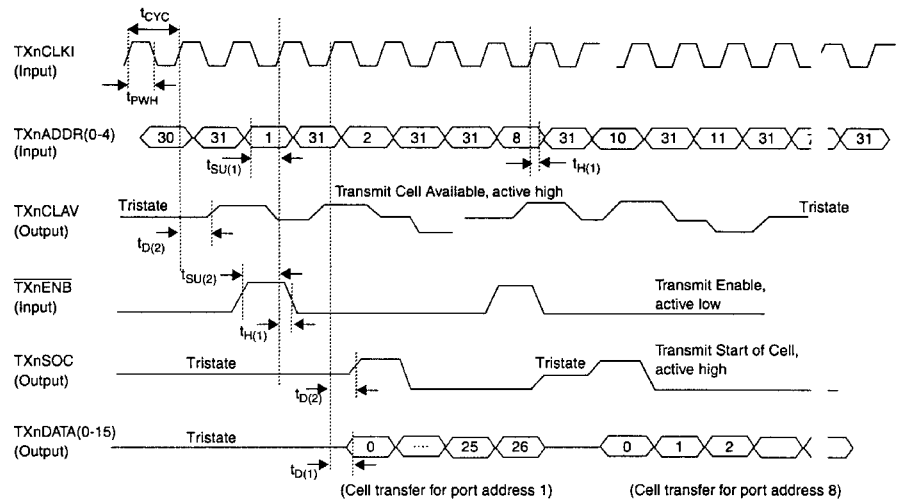

| Parameter | Symbol | Min | Typ | Max | Unit |
|---|---|---|---|---|---|
| TXnCLKI clock cycle time | $t_{CYC}$ | 20 | | | ns |
| TXnCLKI duty cycle, $t_{PWH}/t_{CYC}$ | | 40 | | 60 | % |
| TXnADDR(0-4) setup time to TXnCLKI↑ | $t_{SU(1)}$ | 4.0 | | | ns |
| TXnENB setup time to TXnCLKI↑ | $t_{SU(2)}$ | 7.5 | | | ns |
| TXnENB, TXnADDR(0-4) hold time after TXnCLKI↑ | $t_{H(1)}$ | 1.0 | | | ns |
| TXnDATA(0-15) delay from TXnCLKI↑ | $t_{D(1)}$ | 2.0 | | 11.5 | ns |
| TXnSOC, TXnCLAV delay from TXnCLKI↑ | $t_{D(2)}$ | 2.0 | | 11 | ns |

*PRODUCT PREVIEW*

MICROPROCESSOR INTERFACE TIMING

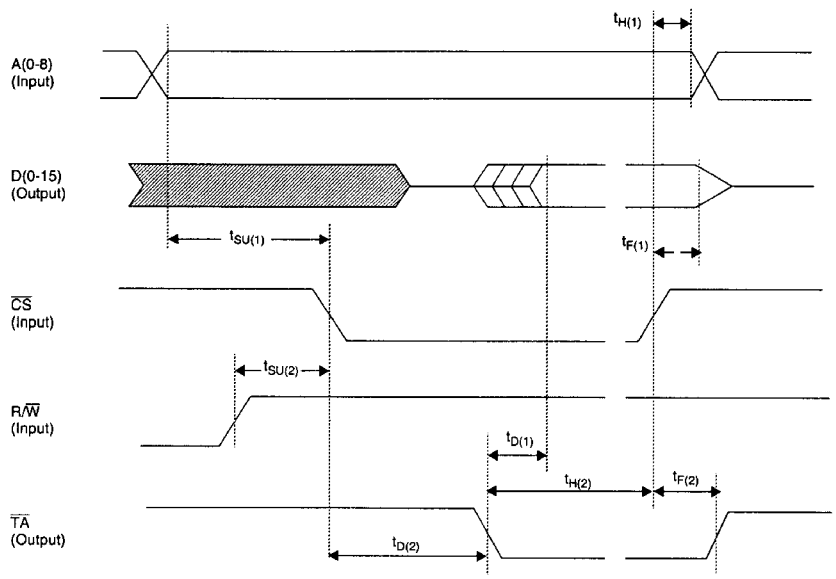

Figure 14. Motorola Microprocessor Read Cycle Timing

| Parameter | Symbol | Min | Typ | Max | Unit |
|---|---|---|---|---|---|
| A(0-8) valid setup time to $\overline{CS}\downarrow$ | $t_{SU(1)}$ | 0.0 | | | ns |
| A(0-8) valid hold time after $\overline{CS}\uparrow$ | $t_{H(1)}$ | 0.0 | | | |
| D(0-15) float time after $\overline{CS}\uparrow$ | $t_{F(1)}$ | 2.0 | | 7.0 | ns |
| D(0-15) valid output delay after $\overline{TA}\downarrow$ | $t_{D(1)}$ | | | 0.0 | ns |
| $\overline{CS}$ hold time after $\overline{TA}\downarrow$ | $t_{H(2)}$ | 5.0 | | | ns |
| R/$\overline{W}$ setup time to $\overline{CS}\downarrow$ | $t_{SU(2)}$ | 0.0 | | | ns |
| $\overline{TA}\downarrow$ delay time from $\overline{CS}\downarrow$ | $t_{D(2)}$ | Note 1 | | | ns |
| $\overline{TA}\uparrow$ float time after $\overline{CS}\uparrow$ | $t_{F(2)}$ | 2.0 | | 12 | ns |

Note:
1. Two cycles of clock PCLK.

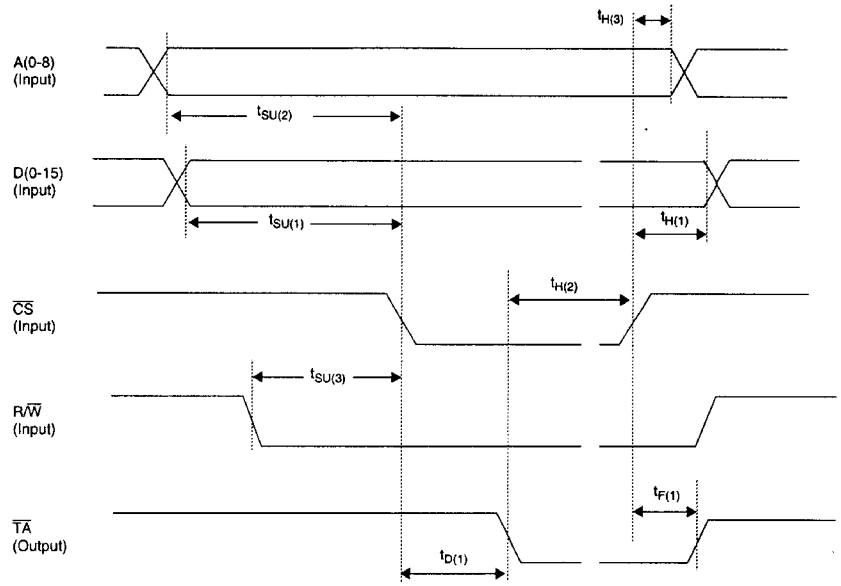

Figure 15. Motorola Microprocessor Write Cycle Timing

| Parameter | Symbol | Min | Typ | Max | Unit |
|---|---|---|---|---|---|
| A(0-8) valid setup time to $\overline{CS}\downarrow$ | $t_{SU(2)}$ | 0.0 | | | ns |
| A(0-8) valid hold time after $\overline{CS}\uparrow$ | $t_{H(3)}$ | 0.0 | | | |
| D(0-15) valid setup time to $\overline{CS}\downarrow$ | $t_{SU(1)}$ | 0.0 | | | ns |
| D(0-15) valid hold time after $\overline{CS}\uparrow$ | $t_{H(1)}$ | 0.0 | | | ns |
| $\overline{CS}$ hold time after $\overline{TA}\downarrow$ | $t_{H(2)}$ | 0.0 | | | ns |
| R/$\overline{W}\downarrow$ setup time to $\overline{CS}\downarrow$ | $t_{SU(3)}$ | 0.4 | | | ns |
| $\overline{TA}\downarrow$ delay after $\overline{CS}\downarrow$ | $t_{D(1)}$ | Note 1 | | | ns |
| $\overline{TA}$ float time after $\overline{CS}\uparrow$ | $t_{F(1)}$ | 2.0 | | 12 | ns |

Note:
1. Two cycles of clock PCLK.

Figure 16. Microprocessor Interrupt Timing
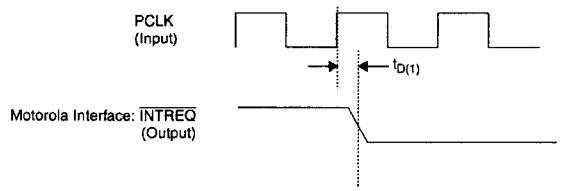
| Parameter | Symbol | Min | Typ | Max | Unit |
|---|---|---|---|---|---|
| INTREQ delay after PCLK↑ | $t_{D(1)}$ | 0.0 | | 14 | ns |

Figure 17. Boundary Scan Timing
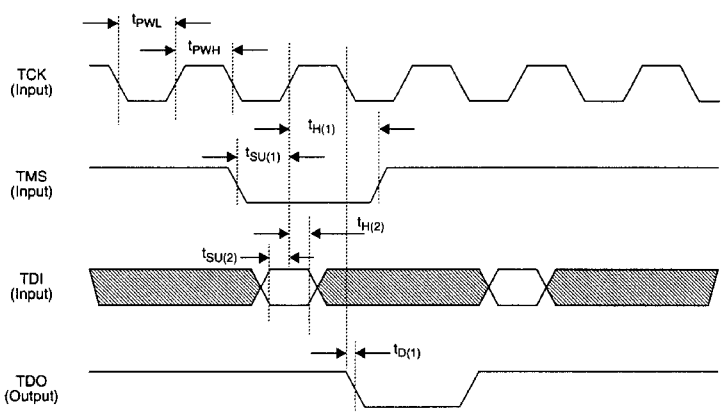
| Parameter | Symbol | Min | Max | Unit |
|---|---|---|---|---|
| TCK clock frequency | - | - | 10 | MHz |
| TCK duty cycle, $t_{PWH}/t_{PWL}$ | - | 40 | 60 | % |
| TMS setup time before TCK↑ | $t_{SU(1)}$ | 3.0 | - | ns |
| TMS hold time after TCK↑ | $t_{H(1)}$ | 1.0 | - | ns |
| TDI setup time before TCK↑ | $t_{SU(2)}$ | 3.0 | - | ns |
| TDI hold time after TCK↑ | $t_{H(2)}$ | 3.0 | - | ns |
| TDO delay from TCK↓ | $t_{D(1)}$ | - | 9.0 | ns |

Proprietary iSwitch Corporation Information for use Sol y its Customers

AsTriX
TXC-05840          DATA SHEET          TRANSWITCH

REGISTER DEFINITION AND HOST ACCESS

GENERAL ACCESS SCHEME

The local host will issue a command to control/configure AsTriX by writing the command register. The local host can choose either polling or interrupt to monitor the status of AsTriX.

The mailbox scheme (TX_MB and RX_MB_H) is basically used for host insertion/extraction, which enables the communication between the local host and a remote device. The mailboxes are also used to assist the register accesses. Each mailbox size is 16*32, or 64-byte to hold one cell.

The RX_MB_L will be used for polling of multicast routing table, chip status, statistics counters, and the TX_MB contents (for debugging). One cell of information held in the RX_MB_L is also referred as a page (64-byte) in the following discussion. There are one page for global (per chip) statistics counters and eight pages for per port status and statistics counter information.

Interrupt scheme will alert the local host for certain condition(s) requiring immediate attention. Each interrupt condition can be masked if the local host chooses to set the corresponding bit in the interrupt mask register.

REGISTER DESCRIPTION

Note: Unless specified, all reserved bits read as '0', write has no effect.

Command Register (R/W):
CMD[15:0]

CMD[15:12]: CMD_CODE, command code (support up to 16 commands)
CMD[11:0]: CMD_PAR, command parameter The local host controls (or configures) the switch chip by writing into the command register. The command will be filtered for its validity, and then be executed. The local host will poll the command execution status register (CMD_EXE) to monitor the command execution status.

It is always recommended that the user should poll the CMD_EXE register to ensure the proper execution of current command before issuance of the next one.

The following types of command will be supported.

*EN_SW:*
Description: Enable (Activate) Switch Chip. Upon issuance of EN_SW command, the AsTriX will go to the ENABLE_MODE from the INIT_MODE. This command is only meaningful in the INIT mode
Command Code: 0x1
Parameter: CMD[2:0], Cell size @ CBI ports
    CMD[2:0] = 000, 52 byte
    CMD[2:0] = 001, 54 byte
    CMD[2:0] = 010, 56 byte
    CMD[2:0] = 011, 58 byte
    CMD[2:0] = 100, 60 byte
    CMD[2:0] = 101, 62 byte
    CMD[2:0] = 110, 64 byte
    CMD[2:0] = 111, 64 byte

TRANSWITCH     DATA SHEET     AsTriX TXC-05840

CMD[3] = 1 / 0, Enable-Parity-Check / Disable-Parity-Check
If parity check disabled, CMD[5:4] will be ignored.

CMD[5:4], Parity Mode (consistent with UUB doc.)
'00' = odd parity over data only
'01' = reserved
'10' = even parity over data only
'11' = reserved CMD[6] = 1/0, standard ATM / non-standard ATM mode
If standard ATM mode, the source port address will be carried in the UDF2 field, the 6th byte of the ATM payload out of the AsTriX port.

CMD[9:7], Multicast bitmap position for non-ATM mode
'000' = the bitmap starts from byte 1 of each multicast cell
'001' = the bitmap starts from byte 3 of each multicast cell
'010' = the bitmap starts from byte 5 of each multicast cell
'011' = the bitmap starts from byte 7 of each multicast cell
'100' = the bitmap starts from byte 9 of each multicast cell
'101' = the bitmap starts from byte 11 of each multicast cell
'110' = the bitmap starts from byte 13 of each multicast cell
'111' = reserved CMD[11:10], Reserved

*RST_SW:*
Description: Software reset. The AsTriX will be forced into RST_MODE mode upon issuance of the command from any of the other three modes.
Command Code: 0x2
Parameter: NA

*INIT_SW:*
Description: Initialize switch chip. This command can be issued in any of the other three modes. But, only the RST_MODE to INIT_MODE transition will activate the auto port number assignment process.
Command Code: 0x3
Parameter: NA

*DIAG_SW:*
Description: Enable diagnostic mode. Upon issuance of DIAG_SW command, the AsTriX will go to the DIAG_MODE from the INIT_MODE. This command is only meaningful in the INIT mode. Command Code: 0x4
Parameter: NA

*Proprietary iSwitch Corporation Information for use Sole y its Customers*

AsTriX
TXC-05840             DATA SHEET             TranSwitch

*EN_PORT:*
Description: Enable a CBI port. Ignored if the addressed CBI is already enabled. This command is only meaningful in the NORMAL mode
Command Code: 0x5
Parameter:
> CMD[11:4],
> These 8-bits represents the timer value to detect the port "Link Drop" condition
> CMD[3:0], represent the port number (0 for CBI-1, ..., 9 for CBI-10)

*DIS_PORT:*
Description: Disable a CBI port (CBI will only bypass all cells when disabled). Ignored if the addressed CBI is already disabled. This command is only meaningful in the NORMAL mode
Command Code: 0x6
Parameter:
> If CMD[11] = 0, Disable one port, CMD[10:4] is ignored
> CMD[3:0], represent the port number (0 for CBI-1, ..., 9 for CBI-10)

> If CMD[11] = 1, Disable all ports, CMD[10:0] is ignored

*CLR_STAT_CNTR:*
Description: Clear/Re-start statistics counter. This command will be used in the NORMAL mode only.
Command Code: 0x7
Parameter:
> CMD[11], Reserved for debugging, user have to write a '0' for this bit otherwise unpredictable behavior will occur.
> CMD[10] = 1, clear all the statistics counters, if this bit is set, CMD[9:0] will be ignored
> CMD[9] = 1/0, clear all (or one) global statistics counters (in BC) / clear all (or one) per port statistics counters (in CBI)
> CMD[8:0], indicates designated counter(s)

> If CMD[9] = 1,
> CMD[8:5], reserved (ignored)
> CMD[4:0] specifies which global statistics counter
> '1_xxxx', clear all the global statistics counters
> '0_0000', clear TTC_GEN
> '0_0001', clear TTC_USD
> '0_0010', clear TTC_UDLV
> '0_0011', clear TTC_MDLV
> '0_0100', TTC_HINS
> '0_0101', TTC_HEXT
> '0_0110', clear TTC_RLY
> '0_0111', reserved
> '0_1000' to '0_1111', reserved > If CMD[9] = 0,
> CMD[8:5] indicates the port number (0 ~ CBI-1, ..., 9 ~ CBI-10), CMD[4:0] specifies which per port statistics counter:
'1_xxxx', clear all the per port statistics counters
'0_0000', clear CONG_UCHP_n counter
'0_0001', clear CONG_UCLP_n counter
'0_0010', clear CONG_MCHP_n counter
'0_0011', clear CONG_MCLP_n counter
'0_0100', clear EG_UC_n counter
'0_0101', clear EG_MC_n counter
'0_0110', clear IG_UC_n counter
'0_0111', clear IG_MC_n counter
'0_1000', clear EG_HOST_n counter
'0_1001', clear IG_HOST_n counter
'0_1010', clear LOSS_HOST_n counter
'0_1011', clear reserved
'0_1100', clear LOSS_UCHP_n counter
'0_1101', clear LOSS_UCLP_n counter
'0_1110', clear LOSS_MCHP_n counter
'0_1111', clear LOSS_MCLP_n counter

PUT_MB:
Description: Send the control cell in the TX_MB to the destination CBI port. The local host will poll the TX_MB register to ensure the completion of the transfer before writing into the TX_MB buffer for next transfer. This command will be meaningful in the NORMAL only.
Command Code: 0x9
Parameter:
    CMD[11], "1" to start PUT_MB procedure (TX_MB buffer reserve)
        "0" to end PUT_MB procedure (TX_MB buffer release)
    CMD[10:4], reserved CMD[3:0], designates the port supposed to receive the cell
    CMD[3:0] = 0000, CBI-1
    CMD[3:0] = 0001, CBI-2
    ......
    CMD[3:0] = 0111, CBI-8
    CMD[3:0] = 1000 - 1111, ignored

GET_MB:
Description: Load the RX mailbox with information of chip status, statistics counters, or current contents of TX_MB buffer, this command also supports the partial read (from RX_MB_L buffer by host) after the RX_MB_L buffer is loaded. The local host will poll the RX_MB register to ensure the completion of the transfer before reading the RX_MB_L buffer. This command will be used in the NORMAL mode only.
Command Code: 0xA
Parameter:
    CMD[11], "1" to start GET_MB procedure (RX_MB_L buffer lock)
        "0" to end GET_MB procedure (RX_MB_L or RX_MB_H buffer release)

If CMD[11] = 0,
CMD[10], "1" for RX_MB_H buffer release, "0" for RX_MB_L release
If CMD[11] = 1, CMD[10] is ignored CMD[9], ignored CMD[8:6], indicates which source (table/register)
'000', for current TX_MB buffer
'001', reserved
'010', reserved
'011', reserved
'100', for per port status and statistics counter page
'101', for per port status and statistics counter page, and clear all per port counters
'110', for global status and statistics counter page
'111', for global status and statistics counter page, and clear all global counters upon read CMD[5:0], further indication of the information source
If CMD[8:6] = '10x', CMD[5:0] indicates which port page (0 for CBI-1, ..., 9 for CBI-10)

SET_WM_OFFSET:
Description: Adjust EG queue water mark offset (on per port basis). This command will be used in NORMAL mode only.
Command Code: 0xB
Parameter:
    If CMD[11] = 1, reset all the watermark offset to the default value,
    CMD[10:0] is ignored If CMD[11] = 0, reset the watermark offset for one port,
CMD[10:7], indicates which CBI port (0 ~ CBI-1, ..., 7 ~ CBI-8)
CMD[6], ignored
CMD[5:0] WM_OFFSET
Represent exact watermark offset value from 6 - 24. WM_OFFSET value less than 6 (or larger than 24) will be treated as 6 (or 24). The default value is 6 upon reset.

This is a per port attribute, which allows smooth flow control with proper WM_OFFSET adjustment. The command will be ignored if
(LOW_WM + WM_OFFSET) > (EG_Q_SIZE - 4), where EG_Q_SIZE = 48

SET_LOW_WM:
Description: Adjust EG queue low (in space) water mark (on per chip basis). This command will be used in NORMAL mode only.
Command Code: 0xC
Parameter:
    CMD[5:0] LOW_WM (in space)
    Represent exact low watermark value from 8 - 38, LOW_WM value less than 8 (or larger than 38) will be treated as 8 (or 38). The default value is 24 upon reset.

The value of WM_LOW represents the number of space (in cell) left in the EG queue, upon which the back pressure signal will be asserted. The value of (WM_LOW + WM_OFFSET) represents the number of space (in cell) left in the EG queue, upon which the back pressure signal is de-asserted after assertion.

LOW_WM is chip attribute determined by a few facts, such as total number of active ports on the looped bus and the algorithm for port fair access of the looped bus, etc. Improper setting of LOW_WM may cause cell loss.

If an improper LOW_WM value causes (LOW_WM + WM_OFFSET) > (EG_Q_SIZE - 4) at a port, the WM_OFFSET will be automatically reset to 6 to avoid the illegal setting.

BIST: (need more discussion)
Description: To enable at-speed Built-In-Self-Test (BIST) in the DIAG_MODE. This command will be used in DIAG_MODE mode only.
Command Code: 0xE
Parameter:
    CMD[2:0] DP_SEL (select the data path under test)
    The value of DP_SEL represents the data path selected under the current BIST test.
    '000' = control cell data path
    '001' = reserved
    '010' = UCHP data path
    '011' = UCLP data path
    '100' = MCHP data path
    '101' = MCLP data path
    '110' = reserved
    '111' = reserved
    CMD[5:3] PTN_SEL (select the payload data pattern)
    The value of PTN_SEL represents the data pattern selected under the current BIST test.
    '000' = All 0x0 pattern
    '001' = All 0xF pattern
    '010' = All 0x5 pattern Proprietary TranSwitch Corporation Information for use Solely by its Customers

AsTriX
TXC-05840                    DATA SHEET                    TRANSWITCH®

'011' = All 0xA pattern
'100' = Incremental
'101' = Decrement
'110' = All 0x00FF pattern (byte alternating)
'111' = All 0xFF00 pattern (byte alternating)
CMD[11:6], reserved Note: Command codes 0x0, 0x8, 0xD and 0xF will be reserved for future use.

Command Execution Status Register (Read only):
CMD_EXE[7:0]

CMD_EXE[7:4]: EXE_STATUS, execution status
CMD_EXE[3:0]: Command Code (copied from command register)

The local host controls (or configures) the switch chip by writing into the command register. The command will be filtered for its validity, and then the command code will be copied into the CMD_EXE[3:0] of the command execution status register. The execution status will be shown in the CMD_EXE[7:4], which is defined as followings:

CMD_EXE[7], Set when the current command process is completed (regardless executed or not executed, with or without error); Also set upon RESET, cleared upon issuance of next command
CMD_EXE[6:5], Indicates the execution status, which is valid only when the done bit is set.
'00', correct execution
'01', illegal command code, command is not executed
'10', command issued @ illegal chip state (mode), command is not executed
'11', Wrong parameter, command ignored
CMD_EXE[4], reserved It is always recommended that the user should poll the CMD_EXE register to ensure the proper execution of current command before issuance of the next one. The new command will be ignored if the done bit CMD_EXE[7] is not set.

Switch Status Registers (Read Only):
SW_STATUS[15:0]

SW_STATUS[1:0]: OP_MODE
'00' ~ Disable mode (RST_MODE)
'01' ~ Initialization mode (INIT_MODE)
'10' ~ Diagnostic mode (DIAG_MODE)
'11' ~ Normal mode (NORMAL_MODE)
For detailed mode description, see the "Switch Operation Mode" section.

SW_STATUS[2]: AUTO_INIT_DONE
SW_STATUS[3]: ATM mode
SW_STATUS[7:4]: Total Port Number (valid when AUTO_INIT_DONE = 1)

Proprietary TranSwitch Corporation Information for use Solely by its Customers

TRANSWITCH DATA SHEET

AsTriX
TXC-05840

*PRODUCT PREVIEW*

SW_STATUS[13:8]: Low watermark of all EG queues (in space)
SW_STATUS[15:14], reserved

Port Enable Registers (Read Only):
PORT_EN[15:0]

This register will be polled by the local host after the issuance of EN_PORT or DIS_PORT command to ensure the realization of the command execution. A "1" indicates the port is currently enabled; a "0" the port is currently disabled.

PORT_EN[0], for CBI-HOST
PORT_EN[1], for CBI-1
PORT_EN[2], for CBI-2
PORT_EN[3], for CBI-3
PORT_EN[4], for CBI-4
PORT_EN[5], for CBI-5
PORT_EN[6], for CBI-6
PORT_EN[7], for CBI-7
PORT_EN[8], for CBI-8
PORT_EN[9:15], reserved

BC Interrupt Registers (Read Only/Clear upon Read):
INT_BC[15:0]: A bit pattern indicating error condition and (or) switch statistic counter overflow. The INTR# is a logic "OR" of all the interrupt events, and will be asserted if not masked.

INT_BC[0], TTC_GEN counter overflow (set upon counter MSB 0 -> 1)
INT_BC[1], TTC_USD counter overflow (set upon counter MSB 0 -> 1)
INT_BC[2], TTC_UDLV counter overflow (set upon counter MSB 0-> 1)
INT_BC[3], TTC_MDLV counter overflow (set upon counter MSB 0-> 1)
INT_BC[4], TTC_RLY counter overflow (set upon counter MSB 0 -> 1)
INT_BC[5], TTC_HINS (host insertion) counter overflow (set upon counter MSB 0 -> 1)
INT_BC[6], TTC_HEXT (host extraction) counter overflow (set upon counter MSB 0 -> 1)
INT_BC[7], reserved
INT_BC[8], reserved
INT_BC[9], reserved
INT_BC[10], reserved
INT_BC[11], Reserved
INT_BC[12], Cell received by RX_MB_H from a CBI port (HOST_XTR)
INT_BC[13], Cell drop @ the CBI-HOST EG queue
INT_BC[14], Auto switch port number assignment completion (AUTO_PASS) in INIT_MODE, or BIST completion (BIST_DONE) in the DIAG_MODE
INT_BC[15], Auto switch port number assignment error (AUTO_PASS) in INIT_MODE, or BIST error (BIST_DONE) in the DIAG_MODE Proprietary TranSwitch Corporation Information for use Solely by its Customers

AsTriX
TXC-05840    DATA SHEET    TRANSWITCH®

CBI Interrupt Registers (Read Only/Clear upon Read):
INT_CBI_n[15:0]: A bit pattern indicating error condition and (or) switch statistic counter overflow, where n = 1 - 8.
The INTR# is a logic "OR" of all the interrupt events, and will be asserted if not masked.

INT_CBI_n[0], CONG_UCHP_n counter half full (Set when counter MSB 0 -> 1)
INT_CBI_n[1], CONG_UCLP_n counter half full (Set when counter MSB 0 -> 1)
INT_CBI_n[2], CONG_MCHP_n counter half full (Set when counter MSB 0 -> 1)
INT_CBI_n[3], CONG_MCLP_n counter half full (Set when counter MSB 0 -> 1)
INT_CBI_n[4], EG_UC_n counter half full (Set when counter MSB 0 -> 1)
INT_CBI_n[5], EG_MC_n counter half full (Set when counter MSB 0 -> 1)
INT_CBI_n[6], IG_UC_n counter half full (Set when counter MSB 0 -> 1)
INT_CBI_n[7], IG_MC_n counter half full (Set when counter MSB 0 -> 1)
INT_CBI_n[8], EG_HOST_n counter half full (Set when counter MSB 0 -> 1)
INT_CBI_n[9], IG_HOST_n counter half full (Set when counter MSB 0 -> 1)
INT_CBI_n[10], Cell loss error at the EG host queue
INT_CBI_n[11], Cell loss error due to improper setting of the low watermark for non host EG queues
INT_CBI_n[12], Parity error @ UTOPIA interface (from UUB)
INT_CBI_n[13], Wrong cell size error @ UTOPIA interface (from UUB)
INT_CBI_n[14], Start of cell error @ UTOPIA interface (from UUB)
INT_CBI_n[15], Link drop @ CBI EG interface (Timeout)

Interrupt Mask Register (Read/Write):
INTM_BC[15:0]
This is a interrupt mask register to match the INT_BC interrupt register. For each interrupt bit, there is a corresponding mask bit. The mask bit can be set to prevent INTR# assertion.
The default value will be 0xF7FF upon reset.

INTM_CBI_n[15:0], where n = 1 - 8
This is a interrupt mask register to match the INT_CBI_n interrupt register. For each interrupt bit, there is a corresponding mask bit. The mask bit can be set to prevent INTR# assertion.
The default value will be 0xFFFF upon reset.

TX Mailbox register (Read only):
TX_MB[7:0]
Along with the PUT_MB command, this register is used for host insertion.

TX_MB[0], TX_MB_LOCK
This bit is useful in the multi-tasking environment.

For host insertion, the host has to ensure the TX_MB_LOCK bit is '0' (the TX_MB buffer is free for use) before writing a 'start PUT_MB' command to reserve the TX_MB buffer.

The TX_MB_LOCK bit will be set to '1' after an issuance of a 'start PUT_MB' command. Once the lock bit is set, it is safe to write the TX_MB buffer (partial write is supported).

The local host will return the TX_MB by issuing a 'end TX_MB' command after finishing the TX_MB writing. The TX_MB_LOCK bit will be cleared by the internal logic only after the 64-byte content in the TX_MB are completely transmitted out of the TX_MB (to the designated CBI port), which frees the TX_MB.

TX_MB[4:1], TX_MB_DST
This is copy of parameter field (CMD[3:0]) of the PUT_MB command to reflect the destination(s) of the current payload.

TX_MB[7:5], reserved

RX Mailbox from Local registers (Read only):
RX_MB_L[15:0]
Along with the GET_MB command, this register is used to retrieve local switch status, statistics counters, TX_MB (loop back) *and multicast routing table.*

RX_MB_L[1:0], {RX_MB_L_VALID, RX_MB_L_LOCK}
These two bits are useful in the multi-tasking environment.

To retrieve a page of status/statistics information from the AsTriX, the host has to ensure the {RX_MB_L_VALID, RX_MB_L_LOCK} is '00' before writing a 'start GET_MB' command to reserve the RX_MB_L buffer.

The RX_MB_L_LOCK bit will be set to '1' after an issuance of the 'start GET_MB' command. The internal logic will manage to deliver the designated page to the RX_MB_L buffer, and set the RX_MB_L_VALID bit. Once the both bits are set, it is save to read the RX_MB_L buffer (partial write is supported).

The local host will return the RX_MB_L buffer by issuing an 'end GET_MB_L' command (see GET_MB command description) after finishing the RX_MB buffer reading, which also clears both bits to '00' to free the RX_MB_L buffer.

RX_MB_L[10:2]: RX_MB_L_SRC
This is copy of parameter field (CMD[8:0]) of the GET_MB command to reflect the source (TX_MB/Global-statistics-counter/Per-port-statistics-counter/*MC-Routing-Table*) of the current payload.

RX_MB_L[15:11]: Reserved

RX Mailbox from remote Host (Read only):
RX_MB_H[7:0]
Along with the GET_MB command, this register is used to receive the control cell from remote host through the CBI ports known as 'host extraction'.

RX_MB_H[0], RX_MB_H_VALID
This bit is useful in the multi-tasking environment.

Proprietary TranSwitch Corporation Information for use Solely by its Customers

AsTriX
TXC-05840                    DATA SHEET                    TRANSWITCH®

The RX_MB_H_VALID bit will be set, and (or) the 'HOST_XTR' interrupt will occur (if not masked) once the RX_MB_H receives a 64-byte cell from one of the CBI port. The host is informed by this event and acquires the source CBI port number by reading the RX_MB_H register, or a INT_CBI_n register.

The local host will subsequently read the RX_MB_H buffer (partial read is supported).

The local host will return the RX_MB_H by issuing an 'end GET_MB_H' command (see GET_MB command description) after finishing the RX_MB_H buffer reading, which also clears the RX_MB_H_VALID bit for the next cell receiving (from a CBI port).

RX_MB_H[4:1]: RX_MB_SRC_H
This represents the port number (0 for CBI-1, ..., 9 for CBI-10), from which the control cell is received for inter-host communication.

RX_MB_H[7:5]: Reserved

Global Switch Statistic counter registers (Read only, Read through RX_MB_L):

Total number of cell generated (TTC_GEN), 32-bit

Total number of used cells (TTC_USD), 32-bit

Total number of Unicast cells delivered (TTC_UDLV), 32-bit
Total number of Multicast cells delivered (TTC_MDLV), 32-bit Total number of relayed cells (TTC_RLY), 32bit Total number of control cells from CBI1 ~ CBI8 (TTC_HEXT), 16-bit
Total number of control cells from host (TTC_HINS), 16-bit

Per Port CBI Status and Statistic counter registers (Read only, Read through RX_MB_L):
CBI Status Registers
CBI_STATUS_n[15:0], n = 1 ~ 8
CBI_STATUS_n[0] = 1/0, ENABLE/DISABLE
CBI_STATUS_n[1] = 1/0, UTOPIA-3/UTOPIA-2
CBI_STATUS_n[7:2], WM_OFFSET
CBI_STATUS_n[15:8], reserved

TranSwitch DATA SHEET

AsTriX TXC-05840

*PRODUCT PREVIEW*

Per Port Statistics Counters

Number of congestion @ uni-cast, high priority queue for EG port n (CONG_UCHP_n), 32-bit
Number of congestion @ uni-cast, low priority queue for EG port n (CONG_UCLP_n), 32-bit
Number of congestion @ multicast, high priority queue for EG port n (CONG_MCHP_n), 32-bit
Number of congestion @ multicast, low priority queue for EG port n (CONG_MCLP_n), 32-bit
(The congestion counter is increased by 1 upon each 0-to-1 transition on back pressure signal)

Number of uni-cast cells leaving EG port n (EG_UC_n), 32-bit
Number of multicast cells leaving EG port n (EG_MC_n), 32-bit Number of uni-cast cells entering IG port n (IG_UC_n), 32-bit
Number of multicast cells entering IG port n (IG_MC_n), 32-bit Number of control cells leaving EG port n from CBI-HOST (EG_HOST_n), 16-bit
Number of control cells entering IG port n to CBI-HOST (IG_HOST_n), 16-bit

REGISTER MAPPING

| Address Offset (Hex) | Register Name | Type | Description | Reset Value |
|---|---|---|---|---|
| 0x0 | REV_ID_L | R/O | Revision/Product ID register (lower 16-bit) | |
| 0x2 | REV_ID_H | R/O | Revision/Product ID register (higher 16-bit) ** | |
| 0x4 | CMD | R/W | Command register | |
| 0x6 | CMD_EXE | R/O | Command execution status register | |
| 0x8 | SW_STATUS | R/O | Switch status register | TBD |
| 0xA | PORT_EN | R/O | Port Enable/Disable register | 0x0000 |
| 0xC | TX_MB | R/O | TX mailbox register for host insertion, or M/C routing table update | |
| 0xE | RX_MB_L | R/O | RX mailbox register to retrieve local register and table information | |
| 0x10 | RX_MB_H | R/O | RX mailbox register for host extraction | |
| 0x12 | INTR_SRC | R/O | Interrupt Source Register | |
| 0x14 | INT_BC | R/O C/R | BC interrupt register | |
| 0x16 | INT_CBI_1 | R/O C/R | CBI-1 interrupt register | |

| | | | | |
|---|---|---|---|---|
| 0x18 | INT_CBI_2 | R/O C/R | CBI-2 interrupt register | |
| 0x1A | INT_CBI_3 | R/O C/R | CBI-3 interrupt register | |
| 0x1C | INT_CBI_4 | R/O C/R | CBI-4 interrupt register | |
| 0x1E | INT_CBI_5 | R/O C/R | CBI-5 interrupt register | |
| 0x20 | INT_CBI_6 | R/O C/R | CBI-6 interrupt register | |
| 0x22 | INT_CBI_7 | R/O C/R | CBI-7 interrupt register | |
| 0x24 | INT_CBI_8 | R/O C/R | CBI-8 interrupt register | |
| 0x26 | reserved | | | |
| 0x28 | reserved | | | |
| 0x2A | INTM_BC | R/W | BC interrupt mask register | |
| 0x2C | INTM_CBI_1 | R/W | CBI_1 interrupt mask register | |
| 0x2E | INTM_CBI_2 | R/W | CBI_2 interrupt mask register | |
| 0x30 | INTM_CBI_3 | R/W | CBI_3 interrupt mask register | |
| 0x32 | INTM_CBI_4 | R/W | CBI_4 interrupt mask register | |
| 0x34 | INTM_CBI_5 | R/W | CBI_5 interrupt mask register | |
| 0x36 | INTM_CBI_6 | R/W | CBI_6 interrupt mask register | |
| 0x38 | INTM_CBI_7 | R/W | CBI_7 interrupt mask register | |
| 0x3A | INTM_CBI_8 | R/W | CBI_8 interrupt mask register | |
| 0x3C | reserved | | | |
| 0x3E | reserved | | | |
| 0x40 – 0x7E | TX_MB_BUF | W/O | TX mailbox buffer (64 byte, or 32 word) | |
| 0x80 – 0xBE | RX_MB_BUF_L | R/O | RX mailbox buffer to retrieve local information (64 byte, or 32 word) | |

| 0xC0 – 0xFE | RX_MB_BUF_H | R/O | RX mailbox buffer for host extraction (64 byte, or 32 word) | |

Note:
** The 32-bit Revision/Product ID register contents is the same as JTAG ID register.

MAILBOX CONTENT PAGE

When using GET_MB command to retrieve the information through RX_MB_L buffer, the contents are organized as a 32-word page (64-byte) in the following format.

The page format for port_n, where n = 1 – 8

Per Port Statistics counter page:

| Address (Hex) | Name | Description |
| --- | --- | --- |
| 0x00 | CBI_STATUS_n[15:0] | CBI status register |
| 0x02 | reserved | |
| 0x04 | reserved | |
| 0x06 | reserved | |
| 0x08 | reserved | |
| 0x10 | CONG_UCHP_n[15:0] | Low 16-bit of congestion counter @ UCHP EG queue |
| 0x12 | CONG_UCHP_n[31:16] | High 16-bit of congestion counter @ UCHP EG queue |
| 0x14 | CONG_UCLP_n[15:0] | Low 16-bit of congestion counter @ UCLP EG queue |
| 0x16 | CONG_UCLP_n[31:16] | High 16-bit of congestion counter @ UCLP EG queue |
| 0x18 | CONG_MCHP_n[15:0] | Low 16-bit of congestion counter @ MCHP EG queue |
| 0x1A | CONG_MCHP_n[31:16] | High 16-bit of congestion counter @ MCHP EG queue |
| 0x1C | CONG_MCLP_n[15:0] | Low 16-bit of congestion counter @ MCLP EG queue |
| 0x1E | CONG_MCLP_n[31:16] | High 16-bit of congestion counter @ MCLP EG queue |
| 0x20 | EG_UC_n[15:0] | Low 16-bit of UC EG cell counter |
| 0x22 | EG_UC_n[31:16] | High 16-bit of UC EG cell counter |
| 0x24 | EG_MC_n[15:0] | Low 16-bit of MC EG cell counter |
| 0x26 | EG_MC_n[31:16] | High 16-bit of MC EG cell counter |
| 0x28 | IG_UC_n[15:0] | Low 16-bit of UC IG cell counter |

| 0x2A | IG_UC_n[31:16] | High 16-bit of UC IG cell counter |
| 0x2C | IG_MC_n[15:0] | Low 16-bit of MC IG cell counter |
| 0x2E | IG_MC_n[31:16] | High 16-bit of MC IG cell counter |
| 0x30 | EG_HOST_n[15:0] | Number of control cell outputs |
| 0x32 | IG_HOST_n[15:0] | Number of control cell inputs |
| 0x34 | reserved | |
| 0x36 | reserved | |
| 0x38 | reserved | |
| 0x3A | reserved | |
| 0x3C | reserved | |
| 0x3E | reserved | |

Global statistics counter information page:

The page format for global status/statistics is as following:

| Address (Hex) | Name | Description |
|---|---|---|
| 0x00 | TTC_GEN[15:0] | Bit 0-15 of total cell counter |
| 0x02 | TTC_GEN[31:16] | Bit 16-31 of total cell counter |
| 0x04 | Reserved | |
| 0x06 | Reserved | |
| 0x08 | TTC_USD[15:0] | Bit 0-15 of total used cell counter |
| 0x0A | TTC_USD[31:16] | Bit 16-31 of total used cell counter |
| 0x0C | Reserved | |
| 0x0E | Reserved | |
| 0x10 | TTC_UDLV[15:0] | Low 16-bit of total UC delivered cell counter |
| 0x12 | TTC_UDLV[31:16] | High 16-bit of total UC delivered cell counter |
| 0x14 | TTC_MDLV[15:0] | Low 16-bit of total MC delivered cell counter |
| 0x16 | TTC_MDLV[31:16] | High 16-bit of total MC delivered cell counter |

| | | |
|---|---|---|
| 0x18 | reserved | |
| 0x1A | reserved | |
| 0x1C | reserved | |
| 0x1E | reserved | |
| 0x20 | TTC_RLY[15:0] | Low 16-bit of total relayed cell counter |
| 0x22 | TTC_RLY[31:16] | High 16-bit of total relayed cell counter |
| 0x24 | reserved | |
| 0x26 | reserved | |
| 0x28 | Reserved | |
| 0x2A | Reserved | |
| 0x2C | TTC_HINS[15:0] | Total cell transmitted from TX mailbox for host insertion |
| 0x2E | TTC_HEXT[15:0] | Total cell received by RX mailbox (RX_MB_H) for host extraction |
| 0x30 | reserved | |
| 0x32 | reserved | |
| 0x34 | reserved | |
| 0x36 | reserved | |
| 0x38 | reserved | |
| 0x3A | reserved | |
| 0x3C | reserved | |
| 0x3E | reserved | |

**AsTriX
TXC-05840   DATA SHEET   TRANSWITCH®**

PACKAGE INFORMATION

The AsTriX device is available in a 640-lead plastic ball grid array (PBGA) suitable for surface mounting, as shown in Figure 18.

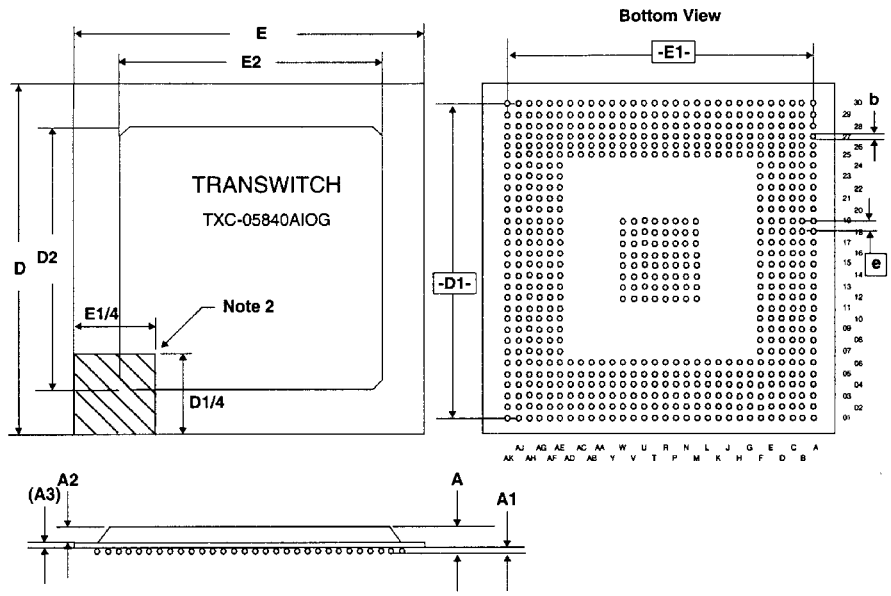

Notes:
1. All dimensions are in millimeters. Values shown are for reference only.
2. Identification of the solder ball A1 corner is contained within this shaded zone. Package corner may not be a 90° angle.
3. Size of array: 30 x 30, JEDEC code MS-034A.

| Dimension (Note 1) | Min | Max |
|---|---|---|
| A | 2.00 | 2.50 |
| A1 | 0.50 | 0.60 |
| A2 | 1.12 | 1.22 |
| A3 (Ref.) | 0.56 | |
| b | .50 | .70 |
| D | 30.80 | 31.20 |
| D1 (Nom) | 29.00 | |
| D2 | 27.95 | 28.70 |
| E | 30.80 | 31.20 |
| E1 (Nom) | 29.00 | |
| E2 | 27.95 | 28.70 |
| e (Ref.) | 1.0 | |

Figure 18. AsTriX TXC-05840 640-Lead Plastic Ball Grid Array Package

*Proprietary TranSwitch Corporation Information for use Solely by its Customers*

TRANSWITCH®      DATA SHEET      AsTriX TXC-05840

*PRODUCT PREVIEW*

ORDERING INFORMATION

Part Number:    TXC-05840AIOG      640-lead Plastic Ball Grid Array Package (PBGA)

RELATED PRODUCTS

Figure 19 illustrates a typical application of the AsTriX *CellBus* Switch device in a generic architecture for ATM access switching. The other related TranSwitch devices are briefly described below:

TXC-05804, CUBIT-3 VLSI Device (Multi-PHY *CellBus* Switch Access Device). A single-chip solution for implementing low-cost ATM multiplexing and switching systems, based on the *CellBus* architecture. Such systems are constructed from a number of CUBIT-3 devices, all interconnected by a 37-line common bus, the *CellBus*. CUBIT-3 supports unicast, broadcast and spatial multicast transfers, and has all necessary functions for implementing a switch: cell address translation, cell routing and outlet cell queuing. This device interfaces with CUBIT-*Pro* devices.

TXC-05805, CUBIT-622 VLSI Device (Multi-PHY *CellBus* Switch Access Device). A single-chip solution for implementing low-cost ATM multiplexing and switching systems, based on the *CellBus* architecture. The CUBIT-622 device is an enhanced version of the CUBIT-3 (TXC-05804) device. The two major enhancements include a throughput increase to 622 Mbit/s and a port density increase to 64 ports. The rate decoupling FIFO have been increased from 4 to 32 cells on ingress to accommodate the higher bandwidth interface.

TXC-05810, ASPEN Device (Multi-Service *CellBus* Switch). ASPEN supports *CellBus* operation in both cell and packet modes via two independent *CellBus* ports. These may be configured to support redundant system operation or alternatively, to provide greater system throughput. Line interface is via UTOPIA 1 or 2 for ATM cells or UTOPIA 2P for variable length packets. Buffering of data traffic and control information, such as connection tables is stored in an external synchronous SRAM.

TXC-05860, Sertopia VLSI Device (UTOPIA Serializer). A single-chip solution for broadband communication systems. The Sertopia device interfaces two remote UTOPIA ports transparently across a serial link. The Sertopia emulates a UTOPIA Level 2 master or UTOPIA Level 2 slave and contains a SERDES (serializer/deserializer) core which transfers the cell or packet chunk along with the UTOPIA port information.

APPLICATION EXAMPLES
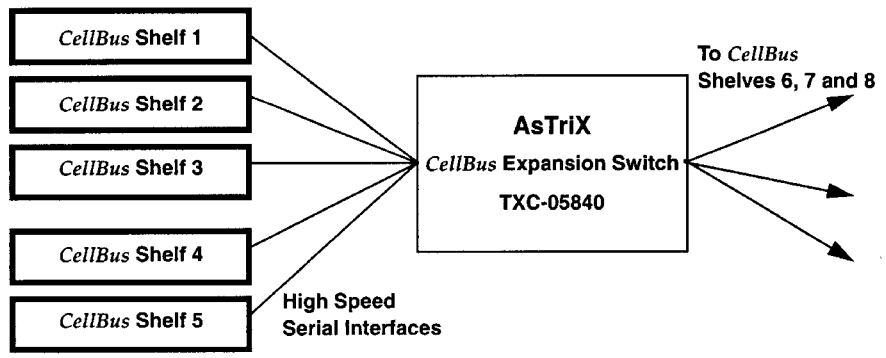
Figure 19. *CellBus* Shelf Aggregation Application Using the AsTriX TXC-05840

T̲RA̲N̲S̲WI̲TCH®  DATA SHEET

AsTriX
TXC-05840

REFERENCE DOCUMENTS

- Medium Access Control Protocol for Single Bus Fair Access Local Area Network, US Patent 5,631,906.
- The ATM Forum: UTOPIA Specification Level 1, Version 2.0.1, March 1994.
- The ATM Forum: UTOPIA Specification Level 2, Version 1.0, June 1995
- MPC860 PowerQUICC™ User's Manual, Motorola 1998.
- MC68360 QUICC User's Manual, Motorola.
- IEEE 1149.1 Standard Test Access Port and Boundary-Scan Architecture, May 1990.

*PRODUCT PREVIEW*

*Proprietary TranSwitch Corporation Information for use Solely by its Customers*

AsTriX
TXC-05840          DATA SHEET          TRANSWITCH®

STANDARDS DOCUMENTATION SOURCES

Telecommunication technical standards and reference documentation may be obtained from the following organizations:

ANSI (U.S.A.):
American National Standards Institute     Tel: (212) 642-4900
11 West 42nd Street                        Fax: (212) 302-1286
New York, New York 10036                   Web: www.ansi.org

The ATM Forum (U.S.A., Europe, Asia):
2570 West El Camino Real                   Tel: (650) 949-6700
Suite 304                                  Fax: (650) 949-6705
Mountain View, CA 94040                    Web: www.atmforum.com ATM Forum Europe Office
Av. De Tervueren 402                       Tel: 2 761 66 77
1150 Brussels                              Fax: 2 761 66 79
Belgium ATM Forum Asia-Pacific Office
Hamamatsu-cho Suzuki Building 3F           Tel: 3 3438 3694
1-2-11, Hamamatsu-cho, Minato-ku           Fax: 3 3438 3698
Tokyo 105-0013, Japan

Bellcore (See Telcordia)

CCITT (See ITU-T)

EIA (U.S.A.):
Electronic Industries Association          Tel: (800) 854-7179 (within U.S.A.)
Global Engineering Documents               Tel: (314) 726-0444 (outside U.S.A.)
7730 Carondelet Avenue, Suite 407          Fax: (314) 726-6418
Clayton, MO 63105-3329                     Web: www.global.ihs.com

ETSI (Europe):
European Telecommunications Standards Institute    Tel: 4 92 94 42 22
650 route des Lucioles                              Fax: 4 92 94 43 33
06921 Sophia Antipolis Cedex                        Web: www.etsi.org
France

*Proprietary TranSwitch Corporation Information for use Solely by its Customers*

TRANSWITCH®     DATA SHEET     AsTriX TXC-05840

*PRODUCT PREVIEW*

GO-MVIP (U.S.A.):

| | |
|---|---|
| The Global Organization for Multi-Vendor Integration Protocol (GO-MVIP) | Tel: (800) 669-6857 (within U.S.A.) |
| | Tel: (903) 769-3717 (outside U.S.A.) |
| 3220 N Street NW, Suite 360 | Fax: (508) 650-1375 |
| Washington, DC 20007 | Web: www.mvip.org |

ITU-T (International):

| | |
|---|---|
| Publication Services of International Telecommunication Union | Tel: 22 730 5111 |
| Telecommunication Standardization Sector | Fax: 22 733 7256 |
| Place des Nations, CH 1211 | Web: www.itu.int |
| Geneve 20, Switzerland | |

MIL-STD (U.S.A.):

| | |
|---|---|
| DODSSP Standardization Documents Ordering Desk | Tel: (215) 697-2179 |
| Building 4 / Section D | Fax: (215) 697-1462 |
| 700 Robbins Avenue | Web: www.dodssp.daps.mil |
| Philadelphia, PA 19111-5094 | |

PCI SIG (U.S.A.):

| | |
|---|---|
| PCI Special Interest Group | Tel: (800) 433-5177 (within U.S.A.) |
| 2575 NE Kathryn Street #17 | Tel: (503) 693-6232 (outside U.S.A.) |
| Hillsboro, OR 97124 | Fax: (503) 693-8344 |
| | Web: www.pcisig.com |

Telcordia (U.S.A.):

| | |
|---|---|
| Telcordia Technologies, Inc. | Tel: (800) 521-CORE (within U.S.A.) |
| Attention - Customer Service | Tel: (908) 699-5800 (outside U.S.A.) |
| 8 Corporate Place | Fax: (908) 336-2559 |
| Piscataway, NJ 08854 | Web: www.telcordia.com |

TTC (Japan):

| | |
|---|---|
| TTC Standard Publishing Group of the Telecommunications Technology Committee | Tel: 3 3432 1551 |
| | Fax: 3 3432 1553 |
| 2nd Floor, Hamamatsu-cho Suzuki Building, | Web: www.ttc.or.jp |
| 1 2-11, Hamamatsu-cho, Minato-ku, Tokyo | |

AsTriX
TXC-05840 DATA SHEET TRANSWITCH

- NOTES -

*Proprietary TranSwitch Corporation Information for use Solely by its Customers*

TranSWITCH® DATA SHEET

**AsTriX
TXC-05840**

- NOTES -

TranSwitch reserves the right to make changes to the product(s) or circuit(s) described herein without notice. No liability is assumed as a result of their use or application. TranSwitch assumes no liability for TranSwitch applications assistance, customer product design, software performance, or infringement of patents or services described herein. Nor does TranSwitch warrant or represent that any license, either express or implied, is granted under any patent right, copyright, mask work right, or other intellectual property right of TranSwitch covering or relating to any combination, machine, or process in which such semiconductor products or services might be or are used.

PRODUCT PREVIEW information documents contain information on products in their formative or design phase of development. Features, characteristic data and other specifications are subject to change. Contact TranSwitch Applications Engineering for current information on this product.

*Proprietary TranSwitch Corporation Information for use Solely by its Customers*

TranSwitch — DATA SHEET — AsTriX TXC-05840

DOCUMENTATION UPDATE REGISTRATION FORM

If you would like to receive updated documentation for selected devices as it becomes available, please provide the information requested below (print clearly or type) then tear out this page, fold and mail it to the Marketing Communications Department at TranSwitch. Marketing Communications will ensure that the relevant Product Information Sheets, Data Sheets, Application Notes, Technical Bulletins and other publications are sent to you. You may also choose to provide the same information by fax (203.926.9453), or by e-mail (info@txc.com), or by telephone (203.929.8810). Most of these documents will also be made immediately available for direct download as Adobe PDF files from the TranSwitch World Wide Web Site (www.transwitch.com).

Name: _____

Company: _____ Title: _____

Dept./Mailstop: _____

Street: _____

City/State/Zip: _____

If located outside U.S.A., please add - Country: _____ Postal Code: _____

Telephone: _____ Ext.: _____ Fax: _____

E-mail: _____

Please provide the following details for the managers in charge of the following departments at your company location.

| Department | Title | Name |
|---|---|---|
| Company/Division | _____ | _____ |
| Engineering | _____ | _____ |
| Marketing | _____ | _____ |

Please describe briefly your intended application(s) and indicate whether you would like to have a TranSwitch applications engineer contact you to provide further assistance:

_____
_____
_____
_____

If you are also interested in receiving updated documentation for other TranSwitch device types, please list them below rather than submitting separate registration forms:

_____  _____  _____  _____  _____  _____  _____
_____  _____  _____  _____  _____  _____  _____

*Please fold, tape and mail this page (see other side) or fax it to Marketing Communications at 203.926.9453.*

*PRODUCT PREVIEW*

What is claimed is:

1. A multiport non-blocking high capacity ATM and packet switch comprising:
   a) a single chip;
   b) an internal unidirectional time slotted looped bus located on said chip;
   c) a bus controller located on said chip and coupled to said bus;
   d) a microprocessor interface on said chip and coupled to said bus; and
   e) a plurality of switch ports on said chip and coupled to said bus, wherein each of said switch ports includes a UTOPIA interface wherein
      each port includes a full duplex interface.

2. A switch according to claim 1, wherein:
   said bus controller continuously generates fixed size time slots to said bus.

3. A switch according to claim 1, wherein:
   said bus controller performs a medium access control protocol for prioritized fair access among all of said switch ports.

4. A switch according to claim 1, wherein:
   said full duplex interface includes a plurality of ingress FIFO buffers and a plurality of egress FIFO queues.

5. A switch according to claim 4, wherein:
   each port includes a counter array coupled to said ingress FIFO buffers and to said UTOPIA interface, said counter arrays being adapted to control UTOPIA input depending on the contents of said ingress FIFO buffers.

6. A switch according to claim 4, further comprising:
   f) a congestion bitmap on said chip and coupled to said UTOPIA interface of each of said ports, wherein
      each port includes a congestion indication means coupled to each of said egress FIFO queues and to said congestion bitmap for indicating a state of congestion in each of said egress FIFO queues, said congestion bitmap being adapted to control UTOPIA input of said UTOPIA interfaces.

7. A switch according to claim 1, wherein:
   said UTOPIA interface are 16-bit mode UTOPIA Level 2 compliant interfaces.

8. A switch according to claim 1, wherein:
   data is transferred over said bus in cells of 80 bytes.

9. A switch according to claim 8, wherein:
   the first 16 bytes of each cell is overhead used for bus access control, address/map fields, and high-speed inter-block communication, and
   the remaining 64 bytes are used to carry payload.

10. A switch according to claim 1, wherein:
    said switch is capable of switching variable length packets.

11. A multiport non-blocking high capacity ATM and packet switch comprising:
    a) an internal bus;
    b) a bus controller coupled to said bus;
    c) a microprocessor interface coupled to said bus;
    d) a plurality of switch ports coupled to said bus, wherein each of said switch ports includes a UTOPIA interface and one of an ingress buffer and an egress queue; and
    e) congestion control means coupled to each of said one of an ingress buffer and an egress queue and to at least one of said UTOPIA interfaces such that said at least one of said UTOPIA interfaces is directed to stop accepting data when one of said one of an ingress buffer and an egress queue is congested, wherein
      each of said switch ports has an ingress buffer,
      said congestion control means is coupled to each of said ingress buffers and each of said UTOPIA interfaces such that a UTOPIA interface associated with a particular switch port is directed to stop accepting data when said ingress buffer associated with said particular switch port is congested.

12. A multiport non-blocking high capacity ATM and packet switch according to claim 11, wherein:
    each of said switch ports has an egress queue,
    said congestion control means is coupled to each of said egress queues and each of said UTOPIA interfaces such that a UTOPIA interface is directed to stop accepting data destined for an egress queue which is congested.

13. A multiport non-blocking high capacity ATM and packet switch according to claim 11, wherein:
    said congestion control means includes an array of counters.

14. A multiport non-blocking high capacity ATM and packet switch according to claim 11, wherein:
    said congestion control means includes a congestion bitmap.

15. A multiport non-blocking high capacity ATM and packet switch according to claim 11, wherein:
    said switch is capable of switching variable length packets.

16. A multiport non-blocking high capacity ATM and packet switch comprising:
    a) an internal bus;
    b) a bus controller coupled to said bus;
    c) a microprocessor interface coupled to said bus;
    d) a plurality of switch ports coupled to said bus, wherein each of said switch ports includes a UTOPIA interface and one of an ingress buffer and an egress queue: and
    e) congestion control means coupled to each of said one of an ingress buffer and an egress queue and to at least one of said UTOPIA interfaces such that said at least one of said UTOPIA interfaces is directed to stop accepting data when one of said one of an ingress buffer and an egress queue is congested, wherein
      each of said switch ports has an egress queue,
      said congestion control means is coupled to each of said egress queues and each of said UTOPIA interfaces such that a UTOPIA interface is directed to stop accepting data destined for an egress queue which is congested.

* * * * *